United States Patent [19]
Malik et al.

[11] Patent Number: 5,654,450
[45] Date of Patent: Aug. 5, 1997

[54] MONOMERS MONO-SUBSTITUTED FLUORINATED OXETANE

[75] Inventors: Aslam A. Malik, Cameron Park; Thomas G. Archibald, Fair Oaks, both of Calif.

[73] Assignee: Aerojet-General Corporation, Sacramento, Calif.

[21] Appl. No.: 539,696

[22] Filed: Oct. 5, 1995

Related U.S. Application Data

[60] Division of Ser. No. 371,914, Jan. 12, 1995, abandoned, which is a continuation-in-part of Ser. No. 206,618, Mar. 7, 1994, abandoned, which is a continuation of Ser. No. 80,614, Jun. 21, 1993, abandoned, which is a continuation of Ser. No. 911,461, Jul. 10, 1992, abandoned.

[51] Int. Cl.$^6$ ............................................. C07D 305/00
[52] U.S. Cl. ............................................................ 549/511
[58] Field of Search ............................................... 549/511

[56] References Cited

U.S. PATENT DOCUMENTS

| | | |
|---|---|---|
| 2,895,921 | 7/1959 | Price . |
| 2,895,924 | 7/1959 | Hudy . |
| 2,895,931 | 7/1959 | Klug . |
| 2,905,647 | 9/1959 | Goddu . |
| 2,909,492 | 10/1959 | Schilling . |
| 3,096,344 | 7/1963 | Case . |
| 3,210,298 | 10/1965 | Weissermel et al. ................. 260/2 |
| 3,347,801 | 10/1967 | Stogryn . |
| 4,097,048 | 6/1978 | Falk et al. . |
| 4,393,199 | 7/1983 | Manser . |
| 4,414,384 | 11/1983 | Berkowitz et al. . |
| 4,483,978 | 11/1984 | Manser . |
| 4,675,452 | 6/1987 | Lagow et al. . |
| 4,707,540 | 11/1987 | Manser et al. . |
| 4,764,586 | 8/1988 | Manser et al. . |
| 4,827,042 | 5/1989 | Lagow et al. . |
| 4,847,427 | 7/1989 | Nappa . |
| 4,864,040 | 9/1989 | Oshaka et al. . |
| 4,898,981 | 2/1990 | Falk et al. . |
| 4,946,992 | 8/1990 | Falk et al. . |
| 4,965,342 | 10/1990 | Vandenberg et al. . |
| 4,970,295 | 11/1990 | Schuchardt . |
| 4,988,797 | 1/1991 | Wardle et al. ..................... 528/408 |
| 5,000,830 | 3/1991 | Marchionni . |
| 5,097,048 | 3/1992 | Falk et al. ........................ 549/511 |

FOREIGN PATENT DOCUMENTS

| | | | |
|---|---|---|---|
| 348350A1 | 12/1989 | European Pat. Off. ...... | C07C 149/18 |
| 430887A3 | 6/1991 | European Pat. Off. ...... | C07D 305/06 |
| 430887A2 | 6/1991 | European Pat. Off. ...... | C07D 305/06 |

OTHER PUBLICATIONS

L. Karam, "Synthese de Diols Telecheliques Halogenes Par Polymerization Cationique D'Oxetanes", Ph.D. Thesis, Ecole Nationale Superieure Chimie, MontPellier, France, pp. 1–22 and 114–147 (1991).

L. Karam, "Thesis Abstract, Ecole Nationale Superieure Chimie", Montpellier, France, pp. 1–4 (1992).

Copies provided in copending 08/371,914 or 08/477,168.

*Primary Examiner*—D. R. Wilson
*Attorney, Agent, or Firm*—Townsend and Townsend and Crew LLP

[57] ABSTRACT

This application is directed to novel fluorinated polymers and prepolymers derived from mono-substituted oxetane monomers having fluorinated alkoxymethylene side-chains and the method of making these compositions. The mono-substituted fluorinated oxetane monomers having fluorinated alkoxymethylene side-chains are prepared in high yield by the reaction of a fluorinated alkoxides with either 3-halomethyl-3-methyloxetane premonomers or aryl sulfonate derivative of 3-hydroxymethyl-3-methyloxetane premonomers. Preparation of a mono-substituted 3-bromomethyl-3-methyloxetane premonomer via a simple, high yield process amenable to commercial scaleup is also disclosed. The fluorinated oxetane monomers of this invention can be readily homo/co-polymerized in the presence of a Lewis acid and polyhydroxy compounds to obtain hydroxy-terminated polyether prepolymers having fluorinated alkoxymethylene side chains. Additionally, the fluorinated oxetane monomers can be copolymerized with non-fluorinated monomers such as tetrahydrofuran to give polyether prepolymers with improved hydrocarbon compatibility. These prepolymers are polydisperse and exhibit number average molecular weights from 5,000 to about 50,000. These prepolymers are amorphous oils with primary hydroxy end-groups and thus function efficiently as the soft block for the synthesis of a variety of thermoset/thermoplastic elastomers and plastics having the characteristics of very low surface energy, high hydrophobicity, low glass transition temperature and low coefficient of friction. The polyurethanes derived from the prepolymers of this invention are elastomeric and, in addition to the above characteristics, exhibit high moisture resistance, high tear strength and excellent adhesion to a variety of substrates.

15 Claims, 2 Drawing Sheets

CONTACT ANGLE WITH TEFLON (110°)

CONTACT ANGLE OF WATER WITH APD - FLUOROPOLYMER (145°)

MONOMERS MONO-SUBSTITUTED FLUORINATED OXETANE

CROSS REFERENCE TO RELATED APPLICATIONS

This Application is a Divisional Application of our parent application Ser. No. 08/371,914, filed Jan. 12, 1995, abandoned which in turn is a Continuation-In-Part application of application entitled "Preparation and Polymerization of Perfluoroalkoxy Alkylene Oxides to Prepare Hydrophobic Ethers", Ser. No. 08/206,618, filed March 7, 1994, now abandoned, which in turn is a Continuation application of application of that same title, Ser. No. 08/080,614, filed Jun. 21, 1993, now abandoned, which in turn is a Continuation application of Ser. No. 07/911,461, filed Jul. 10, 1992, now abandoned.

FIELD

This invention relates to prepolymer compositions and the polymers derived therefrom, oxetane monomers having asymmetric mono-substituted pendant fluorinated alkoxymethylene groups as the prepolymer precursors, methods of preparing the precursor monomers and methods of polymerization of the prepolymers to form fluorinated elastomers. The hydroxy-terminated prepolymers have a polyether backbone and are useful, inter alia, for the preparation of polyurethane elastomers, thermoset plastics and coatings. These compositions exhibit hydrophobic properties, very low surface energies, low glass transition temperatures, low di-electric constants, high abrasion resistance and tear strength, low coefficient of friction, high adhesion and low refractive indices.

BACKGROUND

Fluorinated Elastomers

Fluorinated polymers enjoy widespread use as hydrophobic, oleophobic coatings. These materials exhibit excellent environmental stability, high hydrophobicity, low surface energy and a low coefficient of friction, and are used in a number of applications ranging from non-stick frying pans to optical fiber cladding.

Most fluoropolymers, however, are plastics that are difficult to process, difficult to apply and are unsuitable as coatings for flexible substrates due to their high rigidity. One example of a widely used fluorinated material is Teflon, a polytetrafluoroethylene. Teflon is difficult to process in that it is a rigid solid which must be sintered and machined into its final configuration. Commercial application of Teflon as a coating is complicated by its poor adhesion to a substrate and its inability to form a continuous film. As Teflon is insoluble, application of a Teflon film involves spreading a thin film of powdered Teflon onto the surface to be coated, and thereafter the powdered Teflon is sintered in place resulting in either an incomplete film or having many voids. As Teflon is a hard inflexible plastic, a further limitation is that the substrate surface must be rigid otherwise the Teflon will either crack or peel off.

A limited number of commercial fluoropolymers, such as Viton, possess elastomeric properties. However, these materials have relatively high surface energies (as compared to Teflon), poor abrasion resistance and tear strength, and their glass transition temperatures are still high enough (>0° C. for Viton) to significantly limit their use in low temperature environments.

Accordingly there is a need for fluoroelastomers having hydrophobic properties, a surface energies and coefficients of friction at least equivalent to the fluorinated plastics (such as Teflon). Further, such fluoroelastomers must have high adhesion, high abrasion resistance and tear strength, low index of refraction and a low glass transition temperature so that it is suitable for any foreseeably low temperature environment use. Additionally, there is a need for fluoroelastomers that are easily produced in high yields and easy to use. Currently, there are no fluoroelastomers that satisfy all of these needs.

Premonomers

We have discovered and recognized that the conspicuous absence of fluorelastomers in the art exhibiting all of the above enumerated properties can be understood upon analysis of the upstream end of the current processes for synthesis of fluoropolymers and plastics. The kinds and properties of the premonomers currently used in turn result in the limitations in the properties of the monomers, which further limit the diversity and properties of currently known fluoropolymers and fluoroelastomers.

It is known that a haloalkyl oxetane can be substituted in the 3-position with methyl groups containing energetic functional groups such as nitrato, azide, nitro and difluoroamino. The polymerization of these substituted oxetanes in the presence of polyhydroxy aliphatic compounds produces hydroxy-terminated prepolymers having a polyether backbone with pendant energetic groups.

The use of substituted oxetanes as a starting material for the production of polyethers is not new. However, the theme running through the art is that his-substituted oxetanes are of primary interest and commercial importance. This is understandable in that the bis-haloalkyl oxetane starting material or premonomer is easily produced, whereas the mono-substituted 3-haloalkyl methyl oxetane premonomer is difficult and expensive to produce. There is little teaching in the art for guidance on easy, inexpensive methods of preparation of 3-haloalkyl-3-methyl (mono-substituted) oxetane premonomers or their use in synthesizing mono-substituted fluorinated oxetane monomers.

Bis-haloalkyl oxetane premonomers as a starting material are described in Falk et al. (U.S. Pat. No. 5,097,048). Falk disclose 3,3'-bis perfluoroalkyl oxetane monomers derived from bis-haloalkyl oxetane as a starting material. Reaction of the bis-haloalkyl oxetane with a perfluoroalkyl thiol, a perfluoroalkyl amine, a perfluoroalkanol, or a perfluoroalkyl sulfonamide will produce the 3,3'-bis perfluoroalkyl oxetane monomer described in this reference.

Bis-haloalkyl oxetane premonomers are readily commercially available and their derivatives are fairly well covered in the art. Mono-haloalkyl oxetanes, however, are rarely mentioned in the art, appearing only as an incidental comparison in a more complete investigation of the bis-haloalkyl oxetanes. The lack of teaching regarding the mono-substituted fluorinated alkoxymethylene oxetanes (herein "FOX" compounds for Fluorinated OXetane), and their relative commercial unavailability, is undoubtedly due to the fact that mono-substituted haloalkyl oxetanes are very difficult and expensive to make. Current processes for the production of mono-substituted haloalkyl oxetane premonomers, such as 3-bromomethyl-3-methyloxetane ("BrMMO"), are typified by low yields, long, complicated synthetic schemes and the use of toxic, expensive chemicals to convert 1,1,1-tris(hydroxymethyl)ethane ("TME") into BrMMO.

In these processes, TME is reacted with diethyl carbonate to produce the corresponding cyclic carbonate. This in turn undergoes decarboxylation upon thermal decomposition at 160° C. to provide 3-hydroxymethyl-3-methyloxetane ("HMMO"). The HMMO is converted to the primary chloro compound with carbon tetrachloride and triphenyl phosphine. Reaction of the chloro compound with sodium bromide in methyl ethyl ketone results in $S_N2$ displacement of the chlorine to produce BrMMO. This scheme is commercially impractical in that it is both labor intensive and requires expensive, toxic chemicals. Consequently, these disadvantages have precluded the use of mono-substituted fluorinated oxetane (FOX) monomers that may be derived from mono-substituted haloalkyl oxetanes, such as BrMMO, and production of polymer products thereof.

Accordingly, there is a need for a mono-substituted fluorinated alkoxymethylene oxetane monomer with a fluorinated side-chain capable of producing prepolymers and polymers having desirable properties, such as oil and water repellency, at least comparable to the bis-substituted perfluoroalkyl oxetanes known in the literature. Further, there is also a need for a high yielding reaction pathway for production of the mono-substituted haloalkyl premonomer, characterized by a minimum production of by-products, and a commercial feasibility for high volume, high yield production without the excessive labor and materials costs associated with the currently known processes.

Monomers and Prepolymers

The most important criteria in the development of release (i.e., non-stick), high lubricity coatings is the minimization of the free surface energy of the coating. Free surface energy is a measure of the wettability of the coating and defines certain critical properties, such as hydrophobicity and adhesive characteristics of the material. For most polymeric surfaces the surface energy (dispersion component) can be expressed in terms of the critical surface tension of wetting $\gamma_c$. For example, the surface energy of Teflon (represented by $\gamma_c$) is 18.5 ergs/cm$^2$, whereas that of polyethylene is 31 ergs/cm$^2$. Consequently, coatings derived from Teflon are more hydrophobic and non-stick than those derived from polyethylene. A substantial amount of work has been done by the coating industry to develop coatings with surface energies lower than or comparable to Teflon while at the same time exhibiting superior adhesion characteristics.

The literature teaches that in order to prepare coatings with the desirable low surface energy, the surface of the coating must be dominated by —CF$_3$ groups. Groups such as —CF$_2$—H and —CFH$_2$ increase the surface energy of the material. The importance of the number of fluorine atoms in the terminal group (i.e., the group present on the surface) was demonstrated in Zisman et al., *J. Phys. Chem.*, 1953, 57, 622; ibid. *J. Colloid Sci.*, 1954, 58, 236; Pittman et al., *J. Polymer Sci.*, 1968, 6, 1729. Materials with terminal —CF$_3$ groups exhibited surface energies in the neighborhood of 6 ergs/cm$^2$, whereas similar materials with terminal —CF$_2$H groups exhibited values in the neighborhood of 15 ergs/cm$^2$, more than twice the value for the material with terminal —CF$_3$ groups. Teflon incorporates the fluorine moieties on the polymer backbone and does not contain pendant —CF$_3$ groups. Consequently, Teflon does not exhibit surface energies as low as polymers having terminal perfluorinated alkyl side-chains.

A critical requirement in the production of an elastomer is that the elastomer have large zones, or "soft segments", where little or no crosslinking occurs and where the polymer conformation is such that there is little or no Compaction of the polymer as a result of crystallization. Intermediate of these soft zones are "hard blocks" wherein there may be significant hydrogen bonding, crosslinking and compaction of the polymer. It is this alternating soft block and hard block which gives the polymer its elastomeric properties. The longer the soft segment, the more elastic the elastomer.

We have discovered that an improved route to producing elastomers is to produce homo- or co-prepolymers characterized as non-cross linked, assymetrical, hydroxy-terminated, linear oligomers having from about 10 to about 500 carbons, preferrably 20 to about 200 carbons. These prepolymers substantially retain, their integrity in subsequent polymerizing reactions to provide the soft segment zones of the resulting polymers which, in combination with the hard blocks formed during polymerization, produce good elastomers. We have found that the literature does not have any showing of homo- or co-polymerization of either the bis or the mono-substituted fluorinated alkoxymethylene oxetanes to produce soft segment containing prepolymers required for production of elastomers. Accordingly, there is a need for fluorinated oxetane (FOX) monomers having a side-chain with an omega or terminal perfluorinated alkyl group, which monomers are capable of homo-polymerization or copolymerization to produce the soft segment, herein "FOX prepolymers", necessary for a fluorinated elastomer.

Further, in order for the hydroxy-terminated prepolymer with a fluorinated side-chain (i.e., FOX prepolymers) to be useful, it must have a functionality of at least 2. Presence of non-functional or mono-functional materials in the prepolymers result in coatings with poor mechanical and surface properties. Consequently, these coatings have limited commercial value. Non-functional materials, mainly cyclic tetramers and trimers, are formed during the ring opening polymerization from chain "back-biting". Monofunctional materials, on the other hand are formed due to counter-ion terminations, such as diethyl ether and fluoride ion terminations.

Falk et al. (U.S. Pat. No. 5,097,048) disclose the synthesis of bis-substituted oxetane monomers having perfluoro-terminated alkyl group side chains from bis-haloalkyl oxetane, the glycols having perfluoro-terminated alkyl group side chains derived therefrom, including related thiol and amine linked glycols and dimer diols. Most of the fluorinated side-chains are attached to the glycol unit by either a thio, an amine or a sulfonamide linkage. Only a few of their examples describe glycols with perfluoro-terminated alkoxymethylene side-chains.

Falk et al. (EP 03 48 350) report that their process yields perfluoro-terminated alkoxymethylene neopentyl glycols composed of a mixture of (1) approximately 64% of the bis-substituted perfluoro-terminated alkyl neopentyl glycol, and (2) approximately 36% of a mono-substituted perfluoro-terminated alkyl neopentyl glycol product with a pendant chloromethyl group. Evidently, the mono-substituted product results from incomplete substitution of the second chloride on the bis-chloroalkyl oxetane starting material. Consequently, as noted from the Zisman and Pittman work above, the presence of the —CH$_2$Cl as a side-chain significantly increases the surface energy of coatings made from these polymers thus reducing the hydrophobicity and oleophobicity of the coating.

Not surprisingly, it is understandable that Falk et al. (U.S. Pat. No. 5,097,048) discourages the use of the mono-substituted glycol for the preparation of low surface energy coatings, since the monosubstituted glycol as produced from bis-chloroalkyl oxetanes would necessarily have a residual chloromethyl group still attached to the 3-carbon because of the incomplete substitution of the bis-haloalkyl moieties on the starting material. Accordingly, their teaching that the polymer derivatives from mono-substituted glycols do not produce a coating exhibiting the desired properties, to the same extent as coatings derived from bis-substituted glycols, is premised on a lower free surface energy for the bis-substituted compounds as compared to Falk's mono-substituted compounds (Falk, U.S. Pat. No. 5,097,048, column 1, lines 43–50). However, they ignore the fact that the residual chloromethyl group may serve to increase the free surface energy of the Falk mono-substituted compound more so than the fact it is only mono-substituted in a $R_f$ function.

Moreover, the reference cited by Falk et al., in the '048 patent, *J. Org. Chem.*, 45 (19) 3930 (1980), stating at line 33 that "mono-fluoroalkyl oxetanes containing oxygen have been reported" is misleading in that the reference cited discusses oxetanes substituted with —$CH_2F$ side chains (i.e., (monofluoro)alkyl oxetanes) and not alkoxymethylene side chains with terminal perfluoroalkyl groups. Hence, this reference will not lead to materials with low surface energies and is not relevant to the compounds of this invention.

Falk et al. (U.S. Pat. No. 5,045,624) teaches preparation of dimers with fluorinated side-chains having thio linkages, but not of dimers with fluorinated ether side-chains. This is because his synthesis route for preparing dimers with thio linkages cannot be used for the synthesis of dimers with ether linkages. In other words, Falk et al. does not teach preparation of long chain polyethers with fluorinated ether side-chains.

Falk et al. (U.S. Pat. No. 4,898,981) teaches incorporation of their bis-substituted glycols into various foams and coatings to impart to them the desired hydrophobicity and oleophobicity. Classic polyurethane chemistry shows that while a plastic may form by reaction of Falk's glycols with the diisocyantes, elastomers can not form since there is no long chain soft segment. As noted above, such a soft segment is needed for the formation of an elastomer. Since the Falk et al. compounds are only one or two monomer units long, it is clearly too short to function as a soft segment for the formation of a polyurethane elastomer. In Falk et al., the fluorinated glycol and isocyanate segments alternate, with the fluorinated glycol segments being nearly the same size as the isocyanate segments. It is well known that such a polymer structure will not yield elastomers.

None of the Falk et al. references teach or show a homo-prepolymer or co-prepolymer made from bis-perfluoro-terminated alkoxymethylene oxetanes, nor polyurethanes derived thereform or from the corresponding glycols. All of their polyurethanes are made directly from the thiol linked monomers and dimers and not via a prepolymer intermediate. In the examples provided in Falk et al. (U.S. Pat. No. 5,045,624), particularly where the perfluoro-terminated side-chains are large and for all of the dimers, all have thiol linkages; no ether side-chains are shown. The polyurethanes disclosed by Falk et al. (U.S. Pat. No. 4,898,981) are made from the perfluoro-terminated alkylthio neopentyl glycol. They do not teach, show or suggest producing a polyurethane from the perfluoro-terminated alkoxy neopentyl glycol monomer, nor do they suggest, teach or show the types of prepolymers and polymers that can be prepared from the mono-substituted 3-perfluoroalkoxymethylene-3-methyl oxetanes (i.e., FOX monomers). However, Falk et al. (U.S. Pat. No. 5,097,048) in their Example 12 show a polyether prepolymer prepared from a bis-substituted perfluoroalkylthio oxetane. The prepolymer obtained was a white waxy solid, clearly not an elastomer. No characterization as to nature of the end groups, polydispersivity, equivalent weights, etc. of the the waxy solid was given. Absent such a characterization, it is unknown as to whether Falk et al.s' material may be further reacted with an isocyanate to produce a polyurethane polymer. No examples of the preparation of a polymer from any prepolymer is given.

Manser (U.S. Pat. No. 4,393,199) teaches a method for polymerizing oxetane monomers by employing an initiator/catalyst system composed of an alkyl diol and a Lewis acid catalyst, $BF_3$ etherate. Manser teaches that not all oxetane monomers can be homopolymerized and that the rate of polymerization of bis-substituted oxetane monomers is dependent upon the nature of the substituent at the 3 position on the monomer. Manser does not teach or suggest the polymerization of mono-substituted fluorinated alkoxymethylene oxetanes to produce low viscosity, well defined, difunctional hydroxy-terminated assymetric prepolymers with fluorinated side-chains, nor does he suggest that the prepolymer derived from that polymerization could be cured with diisocyanates to obtain elastomers having exceedingly low surface energies.

Vakhlamova (Chem. Abst. 89:110440p) teaches synthesis of oxetane compounds Substituted at the number 3 carbon of the oxetane with —$CH_2O$—$CH_2$—$CF_2$—$CF_2$—H groups. The terminal alkyl portion of this substituent is thus: —$CF_2CF_2$—H in which the terminal or omega carbon bears a hydrogen atom. As discussed supra, the Zisman and Pittman works shows that the presence of the hydrogen significantly increases the surface energy of the polymer derived from these monomers. Falk et al. (U.S. Pat. No. 5,097,048) also recognizes that surface energy increases with the hydrogen atom on the terminal carbon by stating that "fluoroalkyl compounds which are terminally branched or contain omega-hydrogen atoms do not exhibit efficient oil repellency". Further, Vakhlamova focuses on the bis-substituted monomer as he hydrolyzes and polymerizes only the bis-substituted monomer.

A characteristic of the polymers formed from the polymerization of the bis-substituted oxetanes of Falk et al., and the other proponents of bis-substituted oxetanes is that the resulting products are crystalline solids. The bis side-chains are highly ordered and symmetric. Consequently, they pack efficiently to form a crystalline structure. For example, a prepolymer prepared from 3,3-bis(chloromethyl)oxetane is a crystalline solid that melts in the neighborhood of 220° C. This significantly affects the commercial use of these polymers as either or both mixing and elevated temperatures will be required in order to dissolve or melt the Falk et al. polymer for further polymerization or application.

Polymerization of the bis-substituted perfluorinated alkoxymethylene oxetanes has received little attention in the art. Moreover, the polymers derived from the bis-substituted perfluoroalkylthiol oxetanes are waxy solids and will not function as a soft segment in the preparation of commercially useful elastomers and coatings. Further, the ability of a bis-substituted oxetane monomer to homopolymerize appears to be dependent upon the nature of the side-chain at the 3 carbon with no assurance such polymerization will occur, the difficulty of polymerization apparently being due to the interference by the 3-carbon side-chains. Polymerization, and the products of polymerization, of the bis monomer accordingly are unpredictable and inconsistent.

Accordingly, there is a need in the art for a fluorinated elastomer product having low surface energies and the other properties enumerated above, and a production strategy therefor, beginning with a premonomer production process that is easy and inexpensive, to produce an assymetrical mono-haloalkyl methyl oxetane premonomer, which upon further reaction produces an oxetane monomer having a single fluorinated side-chain, which mono-substituted fluorinated monomer is capable of homopolymerization and copolymerization to produce an essentially non-cross-linked soft segment, difunctional, linear, assymetric prepolymer for further reaction to produce fluorinated elastomers and thermoset plastics, resins and coatings having hydrophobic properties, low surface energy, very low glass transition temperatures, low di-electric constants, high abrasion resistance and tear strength, high adhesion and low refractive indices.

THE INVENTION

Objects

It is among the objects of this invention to provide fluorinated elastomers and thermoset plastics with fluorinated alkoxymethylene side-chains having good hydrophobic properties, low surface energies, very low glass transition temperatures, low di-electric constants, high abrasion resistance and tear strength, high adhesion and low refractive indices;

It is an object of this invention to provide a process for making and using fluorinated elastomers and thermoset plastics with fluorinated alkoxymethylene side-chains having low surface energies, very low glass transition temperatures, low di-electric constants, high abrasion resistance and tear strength, high adhesion and low refractive indices;

It is an object of this invention to provide fluorinated elastomers and thermoset plastics with fluorinated alkoxymethylene side-chains having good hydrophobic properties, low surface energies, very low glass transition temperatures, low di-electric constants, high abrasion resistance and tear strength, high adhesion and low refractive indices from the process of this invention;

It is another object of this invention to provide the compositions in which the fluorinated elastomers and plastics of this invention are used as fouling and ice release coatings, drag reduction coatings, moisture barrier coatings; catheters; artificial prosthesis components such as joints, hearts, and valves; contact lenses; intraocular lenses; films, paints; adhesives; non-transfer cosmetics; water repellent coatings; oil/stain resistant coatings; incindiary binders; lubricants, and the like; and processes for the production End use of such coatings, adhesives, binders and compositions;

It is another object of this invention to provide a hydroxy terminated polyether prepolymer having asymmetric, alkoxymethylene side-chains with terminal perfluorinated alkyl groups for the production of the elastomers and thermoset plastics of this invention;

It is another object of this invention to provide a hydroxy terminated polyether co-prepolymer having asymmetric, mono-substituted fluorinated alkoxymethylene side-chains with terminal perfluorinated alkyl groups and a backbone composed of FOX monomer segments and of tetrahydrofuran (THF) segments for the production of the elastomers and thermoset plastics of this invention;

It is another object of this invention to provide the use of the prepolymers and co-prepolymers of this invention as, and as components, inter alia, in: coating compositions; lubricants; and pump oils which impart hydrophobic properties, low surface energies, low coefficient of friction, very low glass transition temperatures, low di-electric constants, high abrasion resistance and tear strength, high adhesion and low refractive indices to these resins, oils, lubricants and coatings;

It is another object of this invention to provide the process for the production of the hydroxy-terminated fluorinated polyether prepolymer having asymmetric, fluorinated alkoxymethylene side-chains of this invention;

It is another object of this invention to provide processes for the production of hydroxy-terminated fluorinated co-prepolymers having, fluorinated alkoxymethylene side-chains and a backbone composed of FOX monomer segments and THF segments;

It is another object of this invention to provide prepolymer and polymeric products of the processes of homopolymerization and of copolymerization of the FOX monomers of this invention;

It is another object of this invention to provide products of the processes of copolymerization of the FOX monomers of this invention with THF;

It is another object of this invention to provide FOX monomers derived from mono-haloalkyl 3-methyloxetanes, the monomers being mono-substituted at the 3 carbon with a fluorinated alkoxymethylene side-chain for the production of the prepolymers of this invention, and processes for the production, use and polymerization thereof;

It is another object of this invention to provide the product of the processes for production of FOX monomers of this invention;

It is another object of this invention to provide processes for making FOX monomers derived from mono-haloalkyl-3-methyloxetanes, the FOX monomers being mono-substituted at the 3-carbon with a fluorinated alkoxymethylene side-chain for the production of the prepolymers of this invention;

It is another object of this invention to provide a relatively simple and inexpensive process for the production of 3-haloalkyl-3-methyloxetane as a premonomer for the FOX monomers of this invention;

It is another object of this invention to provide products from the processes for the production of 3-haloalkyl-3-methyloxetane as a premonomer of this invention; and Still other objects of the invention will be evident from the Specification, drawings and claims hereof.

| DICTIONARY | |
|---|---|
| Aprotic Solvent: | A solvent that does not donate a proton. |
| BrMMO: | Acronym for 3-bromomethyl-3-methyl oxetane, the preferred premonomer of this invention. |
| Contact Angle: | The obtuse or internal angle between the surface of a liquid and the surface of an object in contact with the liquid. A high contact angle corresponds to high hydrophobicity. |
| FOX Copolymerization: | Reaction of a FOX monomer with a either a different FOX monomer or a non-fluorinated monomer to produce a FOX co-prepolymer. |
| DSC: | Acronym for differential scanning calorimeter, a device used for determining a compunds glass transition temperature. |
| Elastomer: | A polymeric material, such as rubber, which can be stretched under low stress to at least twice its original length and, upon immediate release of the stress, will return with force to its approximate original length. |

DICTIONARY

| | |
|---|---|
| FOX: | Acronym for Fluorinated OXetane. As used in the disclosure of this invention the term "FOX" is normally preceeded by a number; e.g., 3-FOX, 7-FOX, etc. The numerical designation indicates the number of fluorine moieties on the single fluorinated side chain on the 3-carbon of the FOX monomer. |
| GLC: | Acronym for gas-liquid chromatography. A device and method used as a separation technique to determine purity and percent conversion of starting materials. |
| GPC: | Acronym for gel permeation chromatography. A device and method used to determine molecular weight. |
| HEMO: | Acronym for 3-hydroxymethyl-3-methyloxetane, an intermediate in the production of the arylsulfonate oxetane premonomer. |
| FOX Homopolyerization: | Reaction of a FOX monomer with itself to produce a FOX homo-prepolymer. |
| Hydrophobicity: | The degree to which a substance lacks an affinity for, or repels, or fails to absorb water. |
| Lewis Acid | A substance that can accept an electron pair from a base; thus $AlCl_3$ and $BF_3$ are Lewis acids. |
| Mono-substituted Oxetane: | In the context of this invention, broadly a non-bis substituted oxetane compound. More specifically, it refers to the 3-halomethyl-3-methyloxetane premonomers and FOX monomers of this invention where the 3-carbon of the oxetane ring is substituted with only one fluorinated side chain and the other 3-carbon side group is a non-fluorinated moiety; e.g., a methyl or ethyl group. |
| FOX Monomer: | In the context of this invention, a mono-substituted fluorinated oxetane or FOX. |
| Phase Transfer Catalyst: | Effectuates or mediates reactions in a dual-phase heterogeneous reaction mixture. |
| FOX Premonomer: | Those 3-haloalkane-3-methyloxetane compounds which upon reaction with fluorinated alkoxides yields the FOX monomers of this invention. |
| FOX Prepolymer: | A hydroxy terminated, polyether oligomer comprising from about 20 to about 300 FOX or FOX/THF monomer units which, upon reaction with a polyisocyanate will yield polyurethane elastomers. |
| Tetrahydrofuran: | A commercially available 5-membered cyclic ether, abbreviated THF. |
| TME: | Acronym for 1,1,1-tris(hydroxymethyl)ethane, the starting material for the BrMMO premonomer synthesis. |

BRIEF DESCRIPTION OF DRAWINGS

The invention is illustrated in part by reference to the drawings in which.

SUMMARY

Figure 1A:
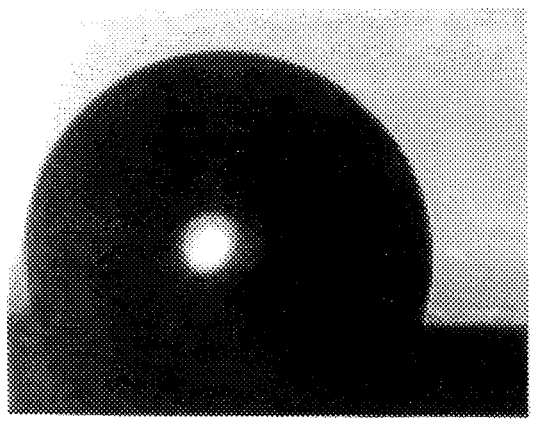
FIG. 1 is a photograph of contact angle of drops of water on a FOX polymer of this invention compared to a Teflon surface.

This invention is directed to mono-haloalkyl oxetane premonomers, mono-substituted oxetanes monomers having fluorinated alkoxymethylene side-chains derived from these premonomers, hydroxy-terminated prepolymers derived from these monomers, and polymers produced from these prepolymers, as well as the synthesis processes associated with each, and the use of the premonomers, monomers, prepolymers and ultimate polymers, both directly and as components of compositions.

The premonomers, monomers, polyether hydroxy-terminated prepolymers and resulting compositions thereof are particularly useful for the preparation of polyurethane elastomers, thermoset plastics and coatings which exhibit a wide variety of useful properties including, interalia, hydrophobic properties, low surface energies, low glass transition temperatures, low dielectric constants, high abrasion resistance and tear strength, low coefficients of friction, high adhesion and low refractive indices. A major application is for non-stick coatings, in that the adhesion of the polymer of this invention is better than Teflon, the surface energy is lower, the application is easier, and the applied film is flexible with good abrasion resistance and tear strength permitting application to both flexible and rigid surfaces. Examples are anti-fouling coatings, ice release coatings, flexible optical fiber cladding, conduit and aqueduct coatings or linings, surface coatings, anti-graffity coatings, automotive top-coat compositions (e.g., car wax), particularly at low temperatures due to low glass transition temperatures on the order of $-40°$ to $-50°$ C. The low index of refraction and good oxygen permeability, coupled with the optical clarity of some of the elastomers produced from the prepolymers make them useful for contact lenses and intraocular lenses. Of course, uses for elastomers are well known, and the improved properties of the elastomers of this invention permit an even wider range of uses.

As noted above, we have discovered an improved route to producing fluorinated elastomers. Our discovery includes an improved, two-step process for the synthesis of a mono-substituted haloalkyl oxetane premonomer which is easier and less expensive than currently known processes. The premonomers in turn are used in another novel process to produce mono-substituted fluoroalkyl oxetanes (FOX monomers). Further, the process is so versatile, that bis-fluoroalkyl oxetanes may be produced by this process in high yields.

The monomers are used to produce homo- or co-prepolymers characterized as non-cross linked, assymetrical, hydroxy-terminated, linear oligomers having from about 10 to about 500 carbons, preferrably 20 to about 200 carbons, i.e., FOX prepolymers. These prepolymers are crucial to the production of fluorinated elastomers in that they substantially retain their integrity in subsequent polymerizing reactions (e.g., reactions with diisocyanates or polyisocyanates) to provide the soft segment blocks of the resulting polymers which, in combination with the hard blocks formed during polymerization, produce good elastomers. While the background does not have any showing of homo- or co-polymerization of either the bis or the mono-substituted fluorinated alkoxymethylene oxetanes to produce prepolymers containing soft segment required for production of elastomers, the processes of our invention will readily polymerize both mono- and bis-substituted FOX monomers. The reaction mechanism of our process will produce prepolymers from bis fluoroalkyl oxetane monomers in high yields as well as from monosustituted FOX monomers.

We have also discovered in the reactions and processes of the background that the presense of two, symmetric side chains, as in the bis-substituted oxetane monomers of Falk et al. result in slower reaction rates and lower yields. Without wishing to be bound by theory, we presently believe this is due to the presense of the two side groups of the bis-monomer compounds sterically hindering the initiation and the propagation reaction of the growing prepolymer chain. Whereas the background shows polymerization of just the thio-linked bis-oxetane monomer (and no ether-linked side-chains) such polymerization is difficult to initate and when successful, results in a prepolymer that is crystalline. The resulting prepolymers are more symmetric and more regular than prepolymers produced from mono-substituted FOX monomers and, therefore, pack more efficiently to form crystalline materials.

Surprisingly, and contrary to the teachings of the prior art, two fluorinated side chains are not necessary to impart high levels of hydrophobic and low surface energy properties. The art teaches that the more fluorine, the better the properties, however, the presense of two identical perfluoroterminated side chains leads to steric hindrance and formation of crystalline materials, a morphology which makes further processing difficult. In contrast, we believe the asymmetry presented by the single (mono) group having fluorinated substituents of the FOX monomers of our invention which upon polymerization prevents the regularity in packing and results in amorphous prepolymers.

Unexpectedly, although the homo- and co-prepolymers composed of FOX monomers and of FOX/THF co-monomers contain less than half of the number of fluorine moieties as a bis-substituted prepolymer, they surprisingly produce polymers that have similar surface energies as a polymer derived from prepolymers having two fluorinated side-chains. Further, even though the FOX/THF prepolymers of our invention contain less fluorine than the FOX prepolymers of our invention, the elastomers produced from the FOX/THF prepolymers surprisingly exhibit surface and physical properties comparable to the elastomers produced from the FOX prepolymers.

We have discovered a polymerization process which virtually eliminates the formation of undesireable by-products. The presence of non-functional or mono-functional materials in the prepolymers result in coatings with poor mechanical and surface properties. Consequently, these coatings have limited commercial value. Non-functional materials, mainly cyclic tetramers and trimers, are formed during the ring opening polymerization from chain "back-biting". Monofunctional materials, on the other hand are formed due to counter-ion terminations, such as diethyl ether and fluoride ion terminations. The processes of this invention are unique in their lack of by-product production. Production of cyclic tetramers and monofunctional prepolymers are almost undetectable.

1. Monomers a) BrMMO Pre-monomer

The FOX monomers of this invention are preferably derived from 3-bromomethyl-3-methyloxetane ("BrMMO"). While the preferred leaving group on the mono-substituted haloalkyl oxetane is bromine, other halogens such as chlorine and iodine, as well as aryl sulfonates may be used. Reaction with BrMMO provides a convenient route in the preparation of 3,3-asymmetrically substituted oxetanes. BrMMO can be converted into a large variety of asymmetrical substituted oxetanes via $SN_2$ displacement with energetic groups such as nitro, nitrato, azido, amino, difluoroamino and nitroamino being introduced. Monomers for polymer radical cure coatings such as oxetanes substituted at the 3-position with vinyl, allyl, homoallyl and styryl groups can also be prepared.

As described in the background, the processes currently practiced for the production of 3-haloalkyl-3-methyl oxetanes, and more particularly to the production of BrMMO, are typified by low yields, side-reaction impurities, long, multi-step synthetic schemes and the use of expensive, toxic chemicals with hazardous materials and hazardous waste handling and disposal problems. These represent significant obstacles in the commercial scale-up of these processes. Consequently, 3-haloalkyl-3-methyl oxetane is not currently commercially available.

The process for the production of BrMMO of this invention, however, uses common inexpensive starting materials and provides BrMMO cleanly in high yields with only two steps. The process is novel in that it incorporates an in-situ generation of HBr. Unexpectedly, the in-situ generation of HBr permits the use of an alcohol with a molecular weight greater than n-butanol to produce a primary bromide in high yield with no by-products.

In the first step, as shown in Formula 1 below, 3-bromo-2-bromomethyl-2-methylpropyl acetate 2 (the dibromoacetate of 1,1,1-tris(hydroxymethyl)ethane or TME) is formed via bromination of the TME in glacial acetic acid with in-situ generated HBr. The HBr is formed in situ from the reaction of sulfuric acid with sodium bromide. Reaction temperature may range from about 100° to about 130° C., preferably about 120° C. We have discovered that the formation of the triacetate of TME unexpectedly more easily undergoes displacement with the bromide ion produced by the in situ generation of HBr. This step is novel in that this is the first time that a primary alcohol (having a molecular weight greater than n-butanol) has been converted in high yield to a primary bromide using a sodium bromide/sulfuric acid process. Further, the in-situ formation of the HBr reagent significantly simplifies the reaction and the concomitant materials handling concerns of such a strong acid were it not so produced. Unexpectedly, the bromination of the TME tri-acetate only produces the TME dibromoacetate. Surprisingly, formation of the mono-bromo and tri-bromo TME derivatives is not observed.

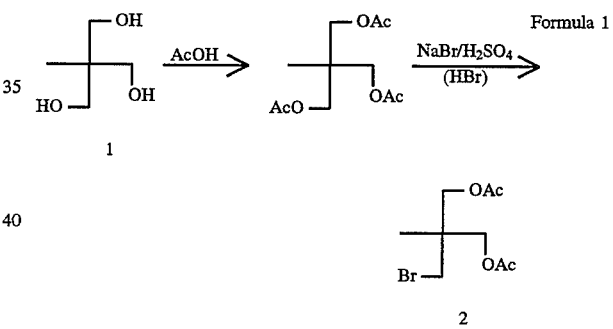

In the second step, see Formula 2 below, the oxetane ring is closed by reacting the TME dibromoacetate with NaOH in refluxing $CCL_4$ (or n-butyl chloride) using a quaternary ammonium salt as a phase transfer catalyst (PTC). The ratio of the PTC to the TME dibromoacetate may range from 0.1 to about 2.0% wt/wt and is preferably 0.5% wt/wt. Upon reflux, the TME dibromo derivative 3 closes to produce the 3-bromomethyl-3-methyloxetane 4. Reaction temperature is dependent upon the reflux temperature and may range from room temperature to about 100° C., preferably from about 70° to about 80° C. An unexpected result of these reaction scheme is the absence of by-products from competing reactions.

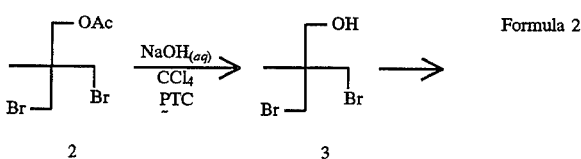

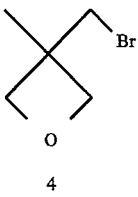

4

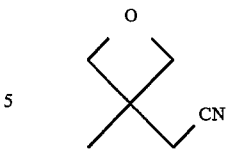

This phase transfer catalyzed intramolecular cyclization has not been attempted before for the production of BrMMO. Prior attempts have resulted in low yields of the cyclic products (12–60%) due to two principle side reactions. The first side reaction is the formation of a stable olefin, 3-bromo-2-methylprop-1-ene, in preference to the relatively more strained oxetane ring. A second competing reaction is the formation of the dimer and trimer.

These side reactions are minimized by choosing an appropriate solvent. We have found that n-butyl chloride and carbon tetrachloride provided yields of BrMMO on the order of 94–97%. Other solvents investigated, such as toluene, ligroine, 1,1,2-trichloroethane, benzene, n-hexane and hexanes gave more complex reaction mixtures containing both competing side reactions of elimination and dimerization.

BrMMO can easily be converted to a large variety of asymmetrically substituted oxetanes via displacement of the primary bromide, an excellent leaving group. These monomers can then be polymerized via Lewis acids to provide polymers with a wide range of applications in energetic and coating materials. Examples of synthesized and possible monomers are listed below.

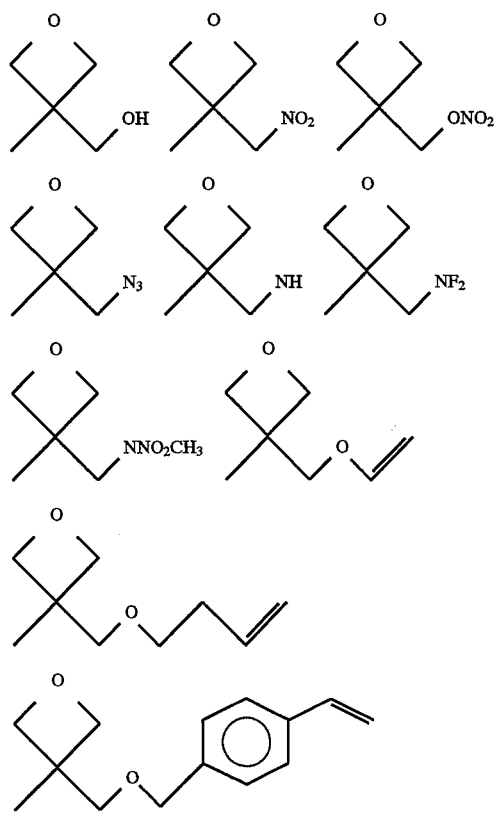

The ability to produce these monomers is dependent upon the clean, high yield process for the formation of BrMMO without the competing side reactions and associated by-products normally associated with this type of reaction. This is due to the unexpected effect of the phase transfer reaction of a base catalyzed internal cyclization of the TME dibromo derivative 3 of Formula 2.

While this discussion has been directed to the synthesis process of BrMMO, the reaction conditions described above can be used to produce a 3-bromomethyl-3-ethyl oxetane using 1,1,1-trimethylol propane ("TMP") as the starting material. Also, this process can be used for the synthesis of other mono-haloalkyl oxetanes such as 3-chloromethyl-3-methyloxetane, 3-iodomethyl-3-methyloxetane, 3-chloromethyl-3-ethyloxetane, etc.

Oxetane Monomers

The BrMMO of this invention may be further processed for the preparation of mono-substituted FOX monomers and prepolymers derived from the homo-polymerization and copolymerization of the FOX monomers.

The incorporation of fluorine in a polymer alters the properties of the resulting polymer:

1. Thermal stability increases thus extending the upper use temperature of the polymer and allows these materials to be processed at higher temperatures without degradation making them suitable for use in environments where other hydrocarbon based polymers cannot be used.
2. Surface energy decreases thus improving the release characteristics of the polymer making it suitable for use as backings for adhesive tapes, release coatings for molds, fouling release coatings for ship hulls, and the like.
3. Refractive index of the resulting polymer is reduced making it useful for optical applications such as contact lenses, intraocular lenses, coatings for optical instruments, cladding for optical fibers, and the like.
4. Coefficient of friction is reduced thus improving the lubricity of the coating making it useful in applications such as vehicle seals, windshield wipers, drag reducing coatings for sail boats, airplanes, etc.
5. Hydrophobicity increases, thus improving water repellency and moisture barrier characteristics making the polymer useful for encapsulating electronic devices, moisture barrier films and coatings, rain erosion coatings, anti-corrosion coatings, etc.
6. Oleophobicity increases, thus making the polymer oil repellent and useful as a stain resistant coating for garments and carpets.
7. Flammability decreases, thus improving flame retardency, for example, on garments coated with the polymer.
8. Environmental stability of the polymer improves, thus making the polymer more stable when exposed to ultraviolet light and moisture.

The mono-substituted fluorinated alkyloxy-3-methyloxetane monomers of this invention have the following formula:

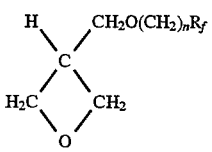

Where:

n is 1 to 3.

R is methyl or ethyl, and $R_f$ is a linear or branched chain fluorinated alkyl and isoalkyl having from 1 to 20 carbons, or an oxaperfluorinated polyether having from 4 to about 60 carbons.

The FOX monomers of this invention are obtained by reaction of aryl sulfonate derivatives of 3-hydroxymethyl-3-methyloxetanes (arylsulfonate-MO) or the reaction of mono-substituted 3-haloalkyl-3-methyloxetanes with fluorinated alkoxides in the presence of a polar aprotic solvent:

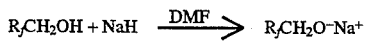

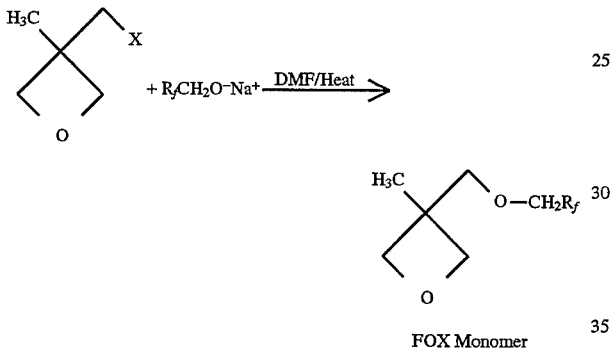

FOX Monomer

Examples of $R_f$:

—CF$_3$, —C$_2$F$_5$, —C$_3$F$_7$, —C$_7$F$_{15}$
3-FOX   5-FOX   7-FOX   15-FOX where:

$R_f$ is linear or branched chain perfluorinated alkyl or isoalkyl having from 1 to 20 carbons, or an oxaperfluorinated polyether having from 4 to about 60 carbons; and X=Br, Cl, I or an aryl sulfonate.

Note that the numeric FOX designation is determined by the number of fluorine atoms in the terminal perfluoroalkyl group of the side-chain.

The aryl sulfonate derivatives of the hydroxyalkyl oxetanes have the general formula:

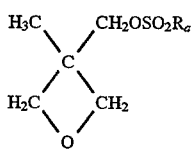

Where:

$R_a$ is monocyclic aryl having from $C_6$ to $C_{10}$ carbons, e.g., benzyl, tolyl, xylyl, mesityl or an alkyl such as —CH$_3$ or —CF$_3$.

The preferred sulfonates are toluene sulfonates, e.g., p-toluene sulfonate derivatives of 3-hydroxymethyl-3-methyloxetane (HMMO).

The fluorinated alkoxides are obtained by the reaction of fluorinated alcohols with sodium hydride in a suitable solvent such as dimethylformamide:

$$R_f(CH_2)_nOH + NaH \longrightarrow R_f(CH_2)_nO^-Na^+ + H_2$$

Although sodium hydride is the preferred base for this reaction, other bases such as potassium hydride, potassium t-butoxide, calcium hydride, sodium hydroxide, potassium hydroxide, NaNH$_2$, n-butyl lithium and lithium diisopropylamide may be used.

The fluorinated alcohols which can be used have the general formula:

$$R_f(CH_2)_nOH$$

wherein:

n is 1 to 3; and $R_f$ is a linear or branched chain fluorinated alkyl or isoalkyl having from 1 to 20 carbons, or an oxaperfluorinated polyether having from 4 to about 60 carbons.

Examples of suitable fluorinated alcohols are: trifluoroethanol, heptafluorobutanol, pentadecafluorooctanol, tridecafluorooctanol, and the like. Other useful alcohols include fluorinated alcohols having the following formulas:

$$HO(CH_2)_n(CF_2)_x—F \qquad \text{a);}$$

$$HOCH_2CF_2(OCF_2CF_2)_x—F \qquad \text{b); and}$$

$$\underset{\underset{F_3C}{|}\phantom{XXX}\underset{CF_3}{|}}{HOCH_2CF(OCF_2CF)_x—F;} \qquad \text{c)}$$

wherein n is 1 to about 3 and x is 1 to about 20.

Whereas the preferred solvent for the formation of the alkoxide from these alcohols is dimethylformamide (DMF), other solvents such as dimethylacetamide, DMSO and hexamethylene phosphoramide (HMPA) may be used.

The pre-monomer of this invention, BrMMO, is particularly well suited for the synthesis of the oxetane monomers in that the BrMMO is uniquely clean and free of by-products resulting from its novel synthetic pathway.

The displacement reaction can be conducted at temperatures ranging from 25° C.–150° C., however, the preferred temperature is between 75° C. and 85° C. At lower temperatures, the rate of displacement may be considered slow and marginally useful for commercial scale-up. At higher temperatures (>120° C.), the rate of displacement is extremely fast. However, at these higher temperatures other side reactions such as hydrolysis of the premonomer to 3-hydroxymethyl-3-methyloxetane dominate. Thus, the preferred reaction temperature is <120° C.

Preferred Process for Synthesis of FOX Monomers

We have recently discovered a preferred process for preparing FOX monomers in high yields that eliminates the use of organic solvents and strong bases, such as NaH. The elimination of organic solvents reduces hazardous waste generation and air emissions of volatile organic compounds. The process steps are as follows:

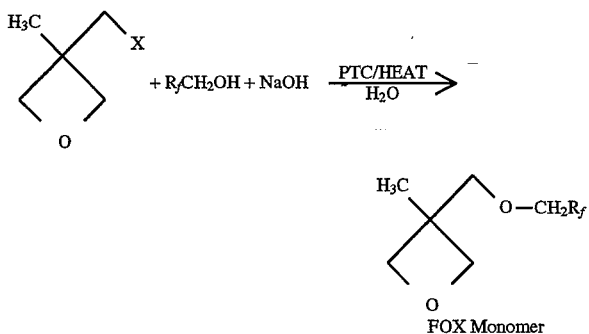

where:
 R$_f$ is linear or branched chain perfluorinated alkyl or isoalkyl having from 1 to 20 carbons, or an oxaperfluorinated polyether having from 4 to about 60 carbons; and
 X=Br, Cl or I.

In this process, a mixture of 3-haloalky-3-methyloxetane, fluoroalcohol, a base such as sodium hydroxide or potassium hydroxide, and a phase transfer catalyst is heated in an aqueous medium at 80°–85° C. until GLC analysis reveals complete consumption of the starting materials. Upon completion of the reaction, the product is recovered by separation and distillation of the organic phase. The organic phase contains most of the FOX monomer. The recovered FOX monomer is polymer grade and has a purity normally in excess of 99%. Isolated yields are high and range from 80% to 90% for the purified FOX monomer. Yields prior to separation and purification exceed 90% for the crude product.

Although a variety of bases such as calcium hydroxide, magnesium hydroxide, tetrabutylammonium hydroxide, etc. can be used for this process, the preferred bases are sodium hydroxide and potassium hydroxide as they are readily available in large quantities and are relatively inexpensive.

Phase transfer catalysts function by transferring the counterion so that it is more soluble in the organic phase. A variety of phase transfer catalysts can be used for this process, such as tetramethylammonium bromide, tetraethylammonium bromide, tetramethylammonium iodide, cetyltributylammonium bromide, crown ethers, glycols, and the like. The preferred catalyst is tetrabutylammonium bromide due to its relatively low cost and good solubility in both organic and aqueous mediums.

The above reaction can be conducted at temperatures as low as 50° C. and as high as 120° C. However, at low temperatures, the rate of displacement is extremely slow and competing side reactions such as hydrolysis start to dominate. At higher temperatures, the rate of displacement is extremely fast requiring specialized equipment that can handle pressure, thus making the process uneconomical and unattractive for commercial scale-up.

The above preferred phase transfer catalyst process is limited to the 3-haloalkyl-3-methyloxetanes and, therefore, precludes using the arylsulfonate derivatives of the 3-hydroxymethyl-3-methyloxetane as starting materials for the synthesis of FOX monomers. This is because arylsulfonates are sensitive towards hydrolysis and under the above phase transfer conditions, hydrolyze readily to form 3-hydroxymethyl-3-methyloxetane, thus resulting in lower yields. This limitation is overcome, however, by the process of this invention which provides high purity 3-bromomethyl-3-methyloxetane in high yields.

2. Prepolymers

There are three types of prepolymers of this invention: Homo-prepolymers where the prepolymer is assembled from only one FOX monomer; Co-prepolymers where the prepolymer is assembled from a mixture of FOX monomers; and FOX/THF co-prepolymers where a FOX monomer (or mixture of FOX monomers) is copolymerized with tetrahydrofuran (THF).

One of the main applications of the hydroxy-terminated, FOX prepolymers is in the development of hydrophobic, non-stick, low friction materials. The most important criteria in preparation of these materials is the minimization of the surface energy, which is a measure of the wettability of the material and defines critical properties such as its hydrophobicity and adhesive characteristics.

In order to prepare materials with low surface energies, it is critical that the fluoroalkyl group is present in the side-chain and that the terminal carbon of the fluoroalkyl group is perfluorinated. The requirement to have fluorine in the side-chain rather than in the polymer backbone is demonstrated by comparing the surface energies of fluorinated polyacrylates and polytetrafluoroethylene (Teflon). Surface energy of Teflon, which contains fluorine in the polymer backbone, is 18.5 ergs/cm$^2$. By comparison, the surface energy of polyfluoroacrylates, which contains fluorine in the side-chains, is between 10–12 ergs/cm$^2$ Also, fluoroalkyl groups that contain hydrogen or halogen (Cl, Br, I) on the terminal carbon have considerably higher surface energies than those with CF$_3$ groups. The dependence of surface energy on the surface constitution of typical organic materials is shown in Table 1.

TABLE 1

| SURFACE ENERGIES OF ORGANIC MATERIALS | |
| --- | --- |
| SURFACE CONSTITUTION | ERGS/CM$^2$ @ 20° C. |
| —CF$_3$ Close Packed | 6 |
| —CF$_2$H | 15 |
| —CF$_2$— | 18 |
| —CH$_3$ | 22 |
| —CH$_2$— | 31 |
| —CH$_2$CHCl— | 39 |
| Polyester | 43 |

It is also preferred to use oxetane monomers substituted at the 3-position with only one perfluoroalkyl group since polymerization of 3,3'-disubstituted oxetane monomers yield prepolymers that are largely crystalline which foreclose preparation of elastomers having the required preoperties. For example, polymerization of 3,3'-bis(chloromethyl)oxetane yields a crystalline polymer that melts at approximately 220° C. Similarly, polymerization of 3,3'-bis(ethoxymethyl)oxetane provides a prepolymer that melts at approximately 80° C.

It should be noted that crystalline prepolymers can not be used in the preparation of polyurethane elastomers. Also, prepolymers from disubstituted FOX monomers contain large amounts of nonfunctional cyclic oligomers, which degrade polymer properties. Surface properties are dependent on the amount of fluorine at the polymer/air interface, and in the case of FOX prepolymers, excellent enrichment of the polymer surface with fluorine is achieved and yet with only one perfluoroalkyl group. Surprisingly, we have discovered that a second fluorinated side chain does not significantly enhance the surface properties, and thus, its introduction in the prepolymer is both not cost effective and forecloses the the fluorinated elastomer field since it introduces crystalline symmetry properties.

We have discovered and recognized that placing the fluorine in the side-chain, rather than on the backbone as in Teflon, improves surface lubricity, and the resulting prepolymer/elastomer exhibits a surface energy lower than a polymer having fluorine in just the backbone. We have discovered, however, that there is a trade-off between having the fluorine on the side-chain versus on the backbone: While we get increased lubricity by incorporating a fluorinated side-chain, there is a reduced thermal stability as compared to a polymer having fluorine only on the backbone, for example Teflon.

Hydroxy Terminated Homo- and Co-prepolymers

The invention also comprises the process of polymerizing FOX monomers, as well as the resultant hydroxy-terminated prepolymers. These prepolymers have the following formula:

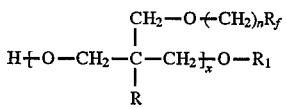

wherein:

n is 1 to 3;

R is methyl or ethyl;

$R_1$ is H or a terminal alkyl alcohol residue having from about 2 to about 5 carbons;

$R_f$ is a linear or branched chain fluorinated alkyl or isoalkyl having from 1 to 20 carbons, or an oxaperfluorinated polyether having from 4 to about 60 carbons; and x is 10 to about 250.

The method of making the FOX homo- and co-prepolymers includes the steps of:

1) charging a reactor with a catalyst, an initiator and a solvent;

2) adding a solution of FOX monomer(s) in an appropriate organic solvent at a temperature between −20° C. and +60° C.;

3) reacting the FOX monomer(s) with the catalyst/initiator solution;

4) quenching the reaction; and 5) separating the FOX prepolymer by precipitation in methanol.

The polymerization can be homopolymerization or copolymerization in which a mixture of two or more of the afore-described oxetane monomers is added to the polymerization zone. A particularly useful copolymerization is block polymerization in which the comonomers are sequentially added in selected proportions to obtain block copolymers of controlled block sizes and properties.

Solution polymerization of the invention may be conducted at a solids concentration of 5%–85%, however the preferred polymerization is normally conducted at a concentration of 50–60% solids. The polymerization is conducted in the presence of a suitable inert solvent, preferably a halogenated $C_1$ to $C_5$ hydrocarbon, e.g., methylene chloride, carbon tetrachloride, chloroform, trichloroethylene, chlorobenzene, ethyl bromide, dichloroethane, fluorinated solvents, etc. with the preferred solvent being methylene chloride, or a mixture of methylene chloride and Freon. Other solvents such as sulfur dioxide, hexanes, petroleum ether, toluene, dioxane and xylene can also be used.

The FOX monomers readily polymerize in the presence of a Lewis acid catalyst (i.e., compounds capable of accepting a pair of electrons) and a polyhydroxy aliphatic compound as a polymerization initiator. Suitable Lewis acids for use as catalysts include: complexes of boron trifluoride, phosphorus pentafluoride, antimony pentafluoride, zinc chloride, aluminum bromide, and the like. The preferred Lewis acid catalyst is a $BF_3$.THF complex.

Suitable initiators are polyhydroxy aliphatic compounds such as alkyl and isoalkyl polyols having from 2 to about 5 carbons and from 2 to 4 hydroxyls, e.g., ethylene glycol, butane-1,4-diol, propylene glycol, isobutane-1,3-diol, pentane-1,5-diol, pentaerythritol, trimethylolpropane, and the like, with the preferred initiator being butane-1,4-diol.

The catalyst and initiator are preferably mixed for 5–10 minutes in the solvent prior to the addition of the FOX monomers. The ratio of catalyst to initiator ranges from 1:1 to 1:5 mol/mol with the preferred ratio being 1:1 to 1:2 mol/mol. An example of a preferred catalyst, initiator and solvent combination is boron trifluoride tetrahydrofuranate, butane-1,4-diol and methylene chloride. The ratio of the monomer to the catalyst ranges from about 10:1 mol/mol to about 300:1 mol/mol, with the preferred range about 50:1 to 100:1 mol/mol.

In a typical example, the catalyst and the initiator are mixed in a solvent prior to the addition of the FOX monomer (s). As oxetane monomers possess relatively high strain energy and undergo exothermic, ring-opening polymerizations, the FOX monomer(s) is added slowly over a period of time to control the reaction temperature and to avoid run-away reactions. The progress of the reaction is monitored by $^1H$ NMR and when >95% of FOX monomer is consumed, the reaction is quenched with water. The prepolymer is purified by precipitation in methanol.

The molecular weight of the prepolymer can be controlled by varying the monomer/catalyst ratio and the reaction temperature. Generally, lower monomer/catalyst ratios and higher reaction temperatures favor the formation of lower molecular weight prepolymers. The ratio of monomer to catalyst can be from 10:1 to 300:1, however, the ratios commonly used range from 50:1 to 100:1 monomer/catalyst.

The reaction temperature can be varied from −20° to +60° C., however, the preferred reaction temperature is +5° C. At higher temperatures, formation of monofunctional materials, mainly —$CH_2F$ terminated materials, is observed. Monofunctional materials can act as chain terminators, thus limiting the molecular weight of the final polymer as well as increasing the polydispersivity. This, in turn, results in polymers having poor mechanical and physical properties.

Cyclic oligomers are normally formed as by-products in the synthesis of polyether prepolymers. These materials are nonfunctional and reduce the usefulness of the prepolymers. Moreover, these materials can leach out of the polymer matrix, and thereby drastically affect the surface and mechanical properties of the polymer. Prepolymers prepared by homopolymerization of FOX monomers contain approximately 2–7% cyclic tetramer.

The $BF_3$-etherate catalyst results in approximately 10%–15% of the mono-functional material and approximately 6%–7% cyclic tetramer by-product.

The preferred catalyst is $BF_3$.THF which results in less than 2% of the cyclic tetramer byproduct and eliminates the formation of the mono-functional prepolymer. In turn, this increases the functionality of the prepolymer and leads to polymers having excellent mechanical, surface and physical properties.

Figure 2:
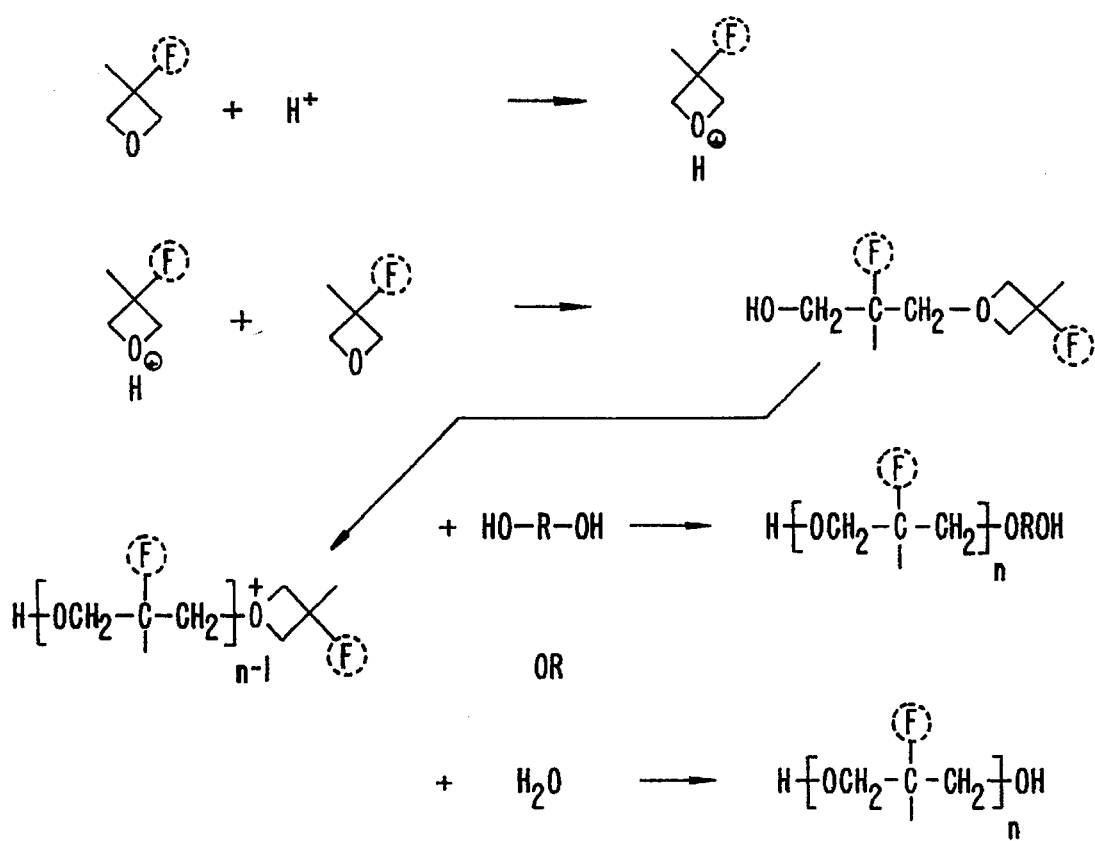
FIG. 2 is a summary of the polymerization reaction of FOX monomers by cationic ring opening reaction.

The polymerization of FOX monomers occurs by cationic ring-opening reaction. The mechanism for which is presented in FIG. 2.

The polymerization is initiated by the proton donated by the initiator, and the protonated oxetane ring undergoes propagation with other oxetanes to generate the polymer chain. The growing polymer chain is then terminated either with alcohol or water to give hydroxy-terminated polyether prepolymers of this invention. It should be noted that the prepolymers of this invention are mixtures of prepolymers resulting from both alcohol and water terminations.

We have discovered through NMR analysis ($^1$H/$^{13}$C) of the prepolymer that the initiator fragment, in particular the butanediol fragment, is located at the end of the polymer chain, and is not incorporated in the middle of the prepolymer backbone. The NMR data ($^1$H/$^{13}$C) clearly shows the presence of a —$CH_2CH_2CH_2CH_2OH$ group which can only occur if the butanediol fragment is present at the end of the prepolymer chain. If the butanediol fragment was incorporated in the middle of the prepolymer, we would see only two peaks corresponding to the symmetrical —$OCH_2CH_2$—$CH_2CH_2O$— group. Our NMR data does not show the presence of this group. While in theory the initiator fragment may be incorporated in the middle of the prepolymer, it is highly unlikely that the bulky, high molecular weight prepolymer will compete efficiently as a chain terminator with a low molecular weight, highly mobile butanediol. The result of the polymerization with the diol initiator is a prepolymer with an unsymmetrical butanediol fraction at the end of the prepolymer chain. Our work is consistent with Conjeevaram et al. (J. of Polymer Science, Vol. 23, 429–444 (1985)) in which 1,4-butanediol is used as an initiator in conjunction with a $BF_3$.etherate to polymerize un-substituted oxetanes. His $^{13}$C NMR analysis also reveals incorporation of the butanediol fragment as the unsymmetrical group —$CH_2CH_2CH_2CH_2OH$ at the end of the polymer chain.

The prepolymers of this invention are amorphous, low Viscosity oils that are easy to process. The inherent viscosity of the prepolymers are between 0.05 and 0.08 dL/g. The number average molecular weights of the prepolymers as determined by gel permeation chromatography, are between 1,000 and 30,000. The polydispersivity, a measure of the spread or "Q" of the molecular distribution, is very low, on the order of less than 5 and typically between 1.1–2.0. The prepolymers exhibited unimodal molecular weight distribution, and were contaminated with approximately 2–7% cyclic tetramer.

It should be noted that molecular weights reported in this invention are expressed relative to well characterized polystyrene standards. The equivalent weight of the prepolymers was determined by $^1$H NMR employing TFAA end group analysis and were between 2,500 and 9,000. The glass transition temperature of the prepolymers, as determined by DSC analysis, was between −38° C. and −45° C.

The structural analysis of the homo- and co-prepolymers of this invention was conducted with $^1$H, $^{13}$C and $^{19}$F NMR spectroscopy. $^1$H NMR analysis revealed the presence of a trimethyleneoxide-based polyether backbone. $^1$H NMR analysis also indicated that when $BF_3$.etherate is used as a catalyst, substantial amounts of mono-functional material with —$CH_2F$ and —$OCH_2CH_3$ end-groups is formed. However, when $BF_3$.THF is used as a catalyst, formation of mono-functional material is not observed. $^1$H NMR was also used to establish the ratio of the two monomers in the co-prepolymer and the identity of the end groups. $^{19}$F NMR analysis confirmed the presence of fluoroalkyl side-chains and the absence of materials with —$CH_2F$ end groups and impurities such as Freon, HF and $BF_3$ catalyst.

$^{13}$C NMR analysis of the co-prepolymers such as poly 3/7-FOX and poly 3/15-FOX, revealed that these materials are random copolymers with little, if any, block structure.

The prepolymers described above are oils that can be used as lubricants or as additives for a variety of applications. For example, these materials can be used as additives in cosmetics to impart water repellency and release characteristics. Also, these materials can be used as additives in engine oils to reduce engine wear and improve performance. The principal application, however, is in the preparation of fluorinated polymers which in turn can be used for diverse applications ranging from car wax to materials for medical and dental applications such as prosthetics and catheter linings.

Co-Prepolymers with Tetrahydrofuran

We have discovered that the fluorinated oxetanes of this invention may be co-polymerized with THF to provide a FOX/THF co-prepolymer having very unique, unexpected characteristics. These are a new class of fluorine containing, hydroxy-terminated, polyether prepolymers, which when cured with polyisocyanates, provide tough polyurethane elastomers that are characterized by low glass transition temperatures and low surface energies. Moreover, these elastomers can be incorporated into coatings that exhibit high abrasion resistance and low coefficient of friction. Combinations of these properties make polymers derived from these fluorinated co-prepolymers extremely attractive for a variety of applications including, but not limited to, anti-fouling (release) coatings; ice release coatings; corrosion resistant coatings, automotive top coats (e.g., car wax), windshield wipers; belt strips; and various household goods; seals and gaskets; encapsulants for electronic devices; oil and dirt resistance coatings; and numerous medical/dental applications.

Tetrahydrofuran (THF) is a five membered cylic ether that is commercially available and is known to polymerize or copolymerize with cationic catalysts but not with anionic catalysts. Attempts to copolymerize THF with cyclic ethers, in particular, oxetanes is unpredictable. Polymerization occurs but the products are often not random copolymers. Due to the vast differences in ring-opening polymerizability between THF and oxetanes, it is more likely that the product is a block copolymer rather than a random copolymer. Poly THF (PTHF) is a semi-crystalline polymer that melts at ca. 50° C., and when employed as the soft segment in urethane elastomers, is likely to crystallize at low temperatures, causing problems with physical properties such as poor flexibility, incomplete or little recovery after elongation, poor modulus, and the like. In a block, or non-random, copolymer, similar problems can occur since THF blocks can crystallize and form semi-crystalline polymers.

In the FOX/THF random coprepolymer of this invention, THF and oxetane segments are randomly spaced along the polymer backbone, thus leading to products that are amorphous oils. The random nature of our co-prepolymers prevents backbone tacticity or any other form of regularity that lends itself to ordering and the development of crystallinity. Hydroxy-terminated polyether prepolymers that are low in crystallinity, preferably amorphous, are particularly suitable as the soft segments for urethane elastomers.

In this invention we describe the copolymerization of FOX monomers with tetrahydrofuran to give FOX/THF coprepolymers. Copolymerization of FOX monomers with THF, not only reduces the cost of fluorinated prepolymers by using less of the relatively more expensive FOX monomers, but also provides prepolymers with superior properties. The co-prepolymers of this invention are random copolymers and are ideal as soft segments for urethane elastomers.

Moreover, these FOX/THF coprepolymers are amorphous oils that are easy to process. Also, the use of THF as a coreactant allows the polymerization to be conducted in bulk and eliminates the use of ozone depleting solvents such as Freons.

The FOX co-prepolymer composition has the following general structure:

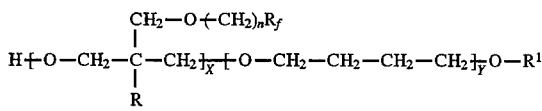

where:

n is 1–3;

R is methyl or ethyl;

$R_f$ is a linear or branched perfluorinated alkyl group having 1–20 carbons, or an oxaperfluorinated polyether having from about 4–20 carbons;

X is 1–100 and Y is 10–150; and $R^1$ is H or an alkyl alcohol residue having from about 2 to 5 carbons.

and:

$M_n$ is 2,000 to 50,000; and $T_g$ is approximately –40° to –42° C.

Unexpectedly, the resulting coprepolymer sequence of this invention is random. The random sequence of the coprepolymer, together with the presence of the assymetric FOX segment, results in a low viscosity oil which significantly facilitates processing and the commercial application of the product.

The surface energy of the FOX/THF coprepolymer as a cured polymer is lower than that of polytetrafluoroethylene (Teflon) and is attributed to the presence of the fluorine in the side-chains rather than the backbone. It is noteworthy that the FOX/THF prepolymer is formed from the mono-substituted FOX monomers of this invention and the surface energy is comparable to that of the polymers formed from the bis-substituted monomers described in the background. Consequently, the FOX monomer is preferable to the bis-perfluoroalkyl monomers of the background, not only because the mono-substituted FOX monomers produce products having comparable or better surface energy, but also because of its ability to copolymerize with THF, thus reducing the starting materials cost. Even though we have significantly reduced the amount of fluorine in the FOX/THF co-prepolymer by introduction of the THF segments, it has thus far been determined that when the FOX/THF copolymer contains up to about 65% THF, no significant reduction in surface energy is observed in polyurethane elastomers as compared to the elastomers prepared from the mono-substituted FOX monomers.

The random nature of the co-prepolymer sequence is wholly unexpected and is achieved with the novel reaction conditions outlined below. The randomness results in an amorphous, low viscosity oil. The benefits of a liquid prepolymer over a crystalline prepolymer (as would be expected for a block copolymer or a prepolymer produced from a bis-substituted monomer) include easier processing and mixing with reactants (e.g., diisocyantes, crosslinkers, chain extenders, etc.).

The method of making the co-prepolymer includes the steps of:

1) premixing THF in an appropriate organic solvent, said THF and solvent temperature between –20° C. and +60° C.;

2) adding a catalyst;

3) adding an initiator;

4) adding a FOX monomer(s); said FOX monomer(s) temperature between –20° C. and +60° C.;

5) quenching the reaction; and 6) separating the FOX/THF prepolymer by precipitation in methanol.

Alternately, where the copolymer ratio of FOX to THF is between the range of 60:40 and 35:65, no organic solvent is required and the prepolymer may be made by addition of FOX to neat THF. The absence of solvent offers significant advantages to manufacturers with respect to the environmental costs associated with solvent hazardous wastes and hazardous materials storage and handling, as well as the lower manufacturing costs and enhanced public perception (i.e., a "green" product). Further, the presence of the hydrocarbon segment (the THF segment), improves solubility of the co-prepolymer in hydrocarbons.

The copolymerization is conducted either in an inert solvent like methylene chloride or Freon 113 or mixtures thereof, or in neat THF. The 90:10 7-FOX/THF co-prepolymer is prepared in a 3:1 mixture of methylene chloride and Freon 113, whereas the 60:40 and 35:65 7-FOX/THF co-prepolymers are prepared in neat THF. Similarly, 50:50 13-FOX/THF and 60:40 15-FOX/THF co-prepolymers are prepared in neat THF. In the synthesis of 90:10 7-FOX/THF co-prepolymer, solvent is used to avoid viscosity build-up during polymerization, and can potentially be eliminated by using high torque mixers. Solution polymerization may be conducted at a solids concentration of 5%–85%, however, polymerization is normally conducted at a concentration of 50–60% solids. Other solvents that can be used for this process are carbon tetrachloride, chloroform, trichloroethylene, chlorobenzene, ethyl bromide, dichloroethane, fluorinated solvents, sulfur dioxide, hexanes, petroleum ether, toluene, dioxane, xylene, etc. with the preferred solvent being methylene chloride, or a mixture of methylene chloride and Freon. The fact that FOX/THF copolymers can be prepared in the absence of a solvent is beneficial in the view of full scale production, since environmental regulations highly restrict the emission of solvents, specially halogenated solvents, into the atmosphere.

The catalyst and the initiator are similar to those used in the homo-polymerization of FOX monomers. Suitable catalysts are Lewis acids i.e., compounds capable of accepting a pair of electrons, example of which include: complexes of boron trifluoride, phosphorous pentafluoride, $SnCl_4$, antimony pentafluoride, etc. Suitable initiators are water and aliphatic alcohols containing 2 to 5 carbons and 1 to 4 hydroxy groups, e.g., trifluoroethanol, methanol, 1,4-butanediol, trimethylolpropane, pentaerythitol, etc.

In a typical example, the catalyst and the initiator are mixed in a solvent prior to the addition of the monomer. THF is a five membered cyclic ether with low strain energy, and does not homopolymerize under the reaction conditions. Thus, THF is added in one shot to the reaction mixture. On the other hand, oxetane monomers possess relatively high strain energy and undergo exothermic, ring-opening polymerizations. Thus, FOX monomers are added slowly over a period of time to control the reaction temperature and to avoid run-away reactions. The progress of the reaction is monitored by $^1H$ NMR and when >95% of FOX monomer is consumed, the reaction is quenched with water. The prepolymer is purified by precipitation in methanol.

The molecular weight of the co-prepolymer can be controlled by varying the monomer/catalyst ratio and the reaction temperature. Generally, lower monomer/catalyst ratios and higher reaction temperatures favor the formation of lower molecular weight co-prepolymers. The ratio of monomer to catalyst can be from 10:1 to 300;1, however, the ratios commonly used are 100:1 monomer/catalyst. The temperature can be from −20° C. to +60° C., however, the preferred reaction temperature is +5° C. At higher temperatures, formation of monofunctional materials, mainly —$CH_2F$ terminated materials, is observed. The +5° C. mean reaction temperature eliminates the formation of —$CH_2F$ terminal groups which are unreactive and would otherwise reduce the functionality of the prepolymer (by formation of the mono-functional product) and lead to polyurethanes with poor mechanical properties.

In contrast to the FOX homo- and co-prepolymers, the formation of cyclic oligomers is not observed in the copolymerization of 7-FOX with >10% mole THF. Similarly, formation of cyclic oligomers is not observed in the preparation of 50:50 13-FOX/THF and 60:40 15-FOX/THF co-prepolymers. A small amount of cyclic tetramer (ca. 1.0%), however, is formed in synthesis of 90:10 FOX/THF co-prepolymer. It is postulated that incorporation of THF in the growing polymer chain changes the number of atoms in the polymer chain and does not allow the chain to bite back and form a thermodynamically stable, 16-membered cyclic ether. This result is especially important in the development of non-toxic fouling release coatings, where discharge of any chemicals from candidate coatings is not acceptable.

The FOX/THF co-prepolymers of this invention are amorphous, low viscosity oils that are easy to process. FOX/THF co-prepolymers are slightly more viscous than FOX homo-prepolymers. The inherent viscosity of a 60:40 7-FOX THF co-prepolymer, determined in THF at 0.5 g/dL concentration, is 0.125 dL/g. By comparison, the inherent viscosity of the 7-FOX homo-prepolymer is 0.072 dL/g. $^1H$ NMR analysis of FOX/THF co-prepolymers indicates that both monomers are incorporated into the co-prepolymer, and that the THF segment is present in the middle of two FOX segments, and not as an end group.

The ratio of the two monomers in the co-prepolymer is established by comparing the area under the peaks corresponding to THF (ca. 1.6 ppm) and 7-FOX (0.93 ppm) segments. $^1H$ NMR analysis also indicates that FOX/THF copolymers are not contaminated with monofunctional materials (—$CH_2F$ terminated) or other impurities. Presence of multiple peaks in the quartenary carbon region of $^{13}C$ NMR, corresponding to the carbon bearing the fluoroalkyl side-chain, reveal that the above prepolymers are random copolymers with little, if any, block structure. $^{19}F$ NMR analysis confirm the presence of the fluoroalkyl side-chain and the absence of —$CH_2F$ end groups, HF and $BF_3$ catalyst. It is important to note that these materials are not block copolymers, since THF blocks could crystallize and lead to materials with increased crystallinity and poor flexibility. This, in turn, would limit the usefulness of FOX/THF materials.

The number average molecular weights of FOX/THF co-prepolymers, as determined by GPC, were between 10,000 and 14,000, whereas polydispersities were between 1.1 and 2.5. The co-prepolymers exhibited unimodal molecular weight distribution, and with the exception of 90:10 7-FOX/THF co-prepolymer, FOX/THF co-prepolymers were free of cyclic oligomers. The equivalent weight of 60:40 7-FOX/THF co-prepolymer, determined by $^1H$ NMR employing TFAA end group analysis, was 6,230. The equivalent weight of the same co-prepolymer by p-toluenesulfonyl isocyanate/dibutyl amine titration method was 5,890. The glass transition temperature of the 60:40 7-FOX/THF co-prepolymer by DSC analysis was −43° C.; no other transitions were detected between −100° C. and +130° C. By comparison, the glass transition temperature of the 7-FOX homo-prepolymer was −42° C. This result indicates that the glass transition temperature of the co-prepolymer is not affected by the incorporation of THF, and that the prepolymer is a random copolymer. If the prepolymer was a block copolymer or a mixture of two homopolymers, more than one transition would be observed. This was further confirmed by the dynamic mechanical property measurements of 60:40 7-FOX/THF co-prepolymer where only one transition ($T_g$) was observed at −41° C. It should be noted that the formation of a random copolymer between FOX and THF monomers is unexpected since the vast difference in the reactivity of these two monomers would dictate the formation of a block copolymer or two homopolymers.

The co-prepolymers described above are oils that can be used as lubricants or as additives for a variety of applications. For example, the co-prepolymers can be used as additives to improve the performance of commercial engine oils or as a lubricant for industrial equipment. The major use of FOX/THF co-prepolymers, however, is in the development of fluorinated polyether urethane elastomers.

3. Polymers

The hydroxy terminated prepolymers of this invention can be used for the synthesis of a variety of polymers such as polyurethanes, polyesters, polycarbonates, polyacrylates, etc. Additionally, the FOX prepolymers of this invention may be used to synthesize novel fluorinated elastomers, thermosets and thermoplastics.

The fluorinated polyurethane elastomers of this invention exhibit the surface properties of fluoropolymers, and the mechanical properties and the processing characterisitics of traditional polyurethanes. These materials exhibit low glass transition temperatures, low coefficient of friction, high abrasion resistance, and extremely low surface energies. In addition, these polymers exhibit excellent mechanical properties and can be processed as thin coatings or into bulk articles. Also fluorinated polyurethane of this invention can be bonded to a variety of substrates. Combination of these properties, make these materials attractive for a variety of applications such as fouling release coatings for ship hulls and other marine structures; drag reducing coatings for ship hulls and aircraft; moisture barrier coatings and encapsulants for electrical circuits; ice release coatings for aircraft and structures; anti-corrosion and protective coatings; coatings for automotive top coats (e.g., car wax), gaskets and seals; backing for adhesive tape; windshield, eyeglass, and window coatings; binders for propellants and flares; bushings for vibration damping; furniture polish; non-transferable, water/oil proof cosmetics; water repellant for fabrics; oil/stain resistant coating for carpets; low friction coating for computer disks and magnetic head rails; and numerous medical/dental applications such as artificial hearts, artificial joints, catheters, contact lenses and intraoccular lenses.

Polyurethanes from FOX Homo-/Co-Prepolymers

The preparation of fluorinated polyurethane elastomers begin with the FOX prepolymers of this invention. As previously described, these prepolymers are amorphous, low viscosity oils that are easy to process. Moreover, these materials are difunctional and possess terminal primary hydroxy groups that react readily with isocyanates to form high molecular weight polyurethane elastomers. Typically, the prepolymer is reacted with an equivalent mount of a polyisocyanate in the presence of a catalyst and a crosslinking agent to form a three-dimensional, poller network. The process involves mixing the components, casting them in a mold, degassing, and curing the mixture at an elevated temperature. Alternately, the FOX prepolymer is reacted with excess diisocyanate and the resulting isocyanate-capped prepolymer is reacted with the crosslinking agent to form the thermoset. If desired, the isocyanate capped-prepolymer can be reacted with a low molecular weight diol or diamine (a chain extender) to form a linear, thermoplastic polyurethane elastomer.

The fluorine-containing thermoset polyurethane elastomer of this invention is composed of repeat units, bounded by cross-linking agents, which have the following structure:

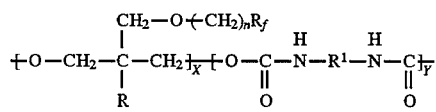

where:

n is 1–3;

R is methyl or ethyl;

$R_f$ is a linear or branched perfluorinated alkyl group having 1–20 carbons, or an oxaperfluorinated polyether having from about 4–20 carbons X is 10–200 and Y is 1–10

$R^1$ is a divalent hydrocarbyl radical, examples of which include the following structures:

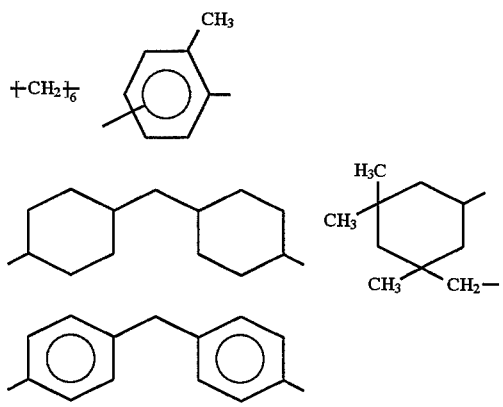

The resulting polyurethane is tack-free, opaque, generally insoluble in organic solvents and has a glass transition temperature between –40° C. and –47° C. Contact angle measurements of between 110° and 145° with distilled water and surface energy measurements of 13.8–15.2 ergs/cm$^2$ indicate that the surface wettability and non-adhesive characteristics of the elastomer of this invention are greater than those measured for Teflon (110° contact angle and 18.5 ergs/cm$^2$ surface energy). We have observed that as the size of the side-chain on the FOX polymers increases, hydrophobicity increases as well (see Table 3). As indicated above, the 145° contact angle of the polyurethane derived from the 15-FOX prepolymer is characteristic of the extreme hydrophobicity of the FOX polymers of this invention. The 145° contact angle of the 15-FOX polyurethane is one of the highest ever observed.

Figure 1B:
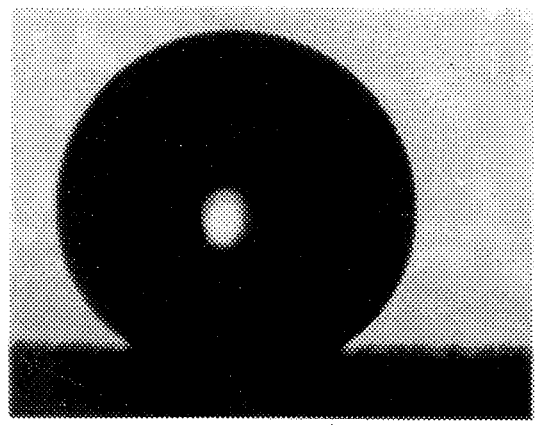

FIG. 1 shows the contact angle of a drop of doubly distilled water on the 15-FOX polyurethane of this invention as compared to the contact angle of a doubly distilled drop of water on Teflon.

The polyurethanes of this invention exhibit the following novel set of characteristics:

1) Elastomeric properties;
2) More hydrophobic and non-stick than Teflon;
3) Processable into thin coatings or bulk articles;
4) Flexible down to about –50° C.;
5) Bondable to a variety of substrates; and
6) Useful ambient temperature range from about –50° C. to about 240° C.

Glass transition temperature is the temperature at which the poller is transformed from a brittle glass to a flexible elastomer. Thus, it dictates the lower use temperature of the elastomer. The glass transition temperatures of non-plasticized FOX polyurethanes, as measured with a differential scanning calorimeter (DSC), are between –40° C. and –47° C. Normally, a plasticizer is used to impart flexibility and to lower the glass transition temperature of polymers. If desired fluorinated plasticizers such as Fomblin, Alfunox, and Kel-F oils can be used to improve the low temperature flexibility of FOX polyurethane elastomers.

Contact angle is the obtuse angle of a water droplet on the polymer surface and reflects the wettability of the polymer surface. A water droplet does not spread on a hydrophobic surface and will exhibit a high contact angle, indicating non-wetting characteristics of the polymer surface. The static contact angle of FOX polyurethanes with doubly distilled water were measured with a Goniometer, and were found to be between 110° and 145°. In sharp contrast, Teflon exhibits a contact angle of 110°. Surface energy is also an important measure of wettability of the polymer surface and defines critical properties such as its hydrophobicity and adhesive characterisitics. Materials with low surface energies are difficult to wet and thus exhibit excellent release characteristics. Teflon, for example, exhibits a surface energy of 18.5 ergs/cm$^2$, and is widely used in preparation of non-stick cooking utensils. Surface energies of common polymers are listed in Table 2. The surface energies of polyurethanes prepared from Poly 3/7 FOX (25:75) and Poly7-FOX are 15.2 and 13.8 ergs/cm$^2$, respectively. These values are considerably lower than that of Teflon and other commercial polymers, indicating that FOX polyurethanes have superior release characterisitics to Teflon. This makes the cured elastomer of this invention more suited than Teflon for those applications where lower wettability and enhanced released characteristics are desired in a coating material.

TABLE 2

| SURFACE ENERGIES OF COMMERCIAL POLYMERS | |
|---|---|
| MATERIAL | SURFACE (ERGS/CM$^2$) |
| Teflon | 18.5 |
| Polydimethylsiloxanes | 24 |
| Polyethylene | 31 |
| Polytrichlorofluoroethylene | 31 |
| Polystyrene | 33–35 |
| Poly(methyl-methacrylate) | 33–34 |
| Nylon 66 | 46 |

The method of making the polyurethane elastomer includes the steps of:

1) Premixing a FOX prepolymer with a polyisocyanate at a reagent temperature between 25° C. and 100° C.;
2) Adding a catalyst;
3) Adding from about 0% to 15% wt/wt of a cross-linking agent;
4) Mixing the components;
5) Casting the components into a mold;

6) De-gassing the cast compound; and
7) Curing the compound mixture at a temperature of between 17° C. and 150° C.

Normally, molar equivalent mounts of FOX prepolymer, crosslinking agent and polyisocyanate are used. However, where the FOX prepolymer is added to an excess of polyisocyanate, an isocyanate-capped prepolymer is produced which may be further reacted with a cross-linking agent to produce a thermoset polyurethane elastomer. Alternately, the isocyanate-capped prepolymer can be reacted with a low molecular weight chain extender such as a diol or divine to prepare linear thermoplastic polyurethane elastomers.

The crosslinking agents normally used are low molecular weight polyols or polyamines such as trimethylolpropane, pentaerythitol, Isonol 93, trimethylolethane, triethanolamine, Jeffamines, 1,4-butanediamine, xylene diamine, diethylenetriamine, methylene dianiline, diethanolamine, etc. The preferred crosslinking agents are trimethylolpropane, Isonol 93, methylene dianiline, and Jeffamines. The mechanical properties of an elastomer can be altered by varying the amount of crosslinking agent. Generally, increasing the amount of crosslinking agent in a polyurethane formulation leads to materials with higher modulus and improved chemical and abrasion resistance. The amount of crosslinking agent can be varied from 0–15% by weight, however, the preferred amount is between 1.5% and 5% by weight.

The preferred catalyst is dibutyltin dilaurate, however, a variety of catalysts such as triethyl amine, triethylene diamine, triphenyl bismuth, chromium acetylacetonate, lead octonate, ferric acetylacetonate, tin octanoate, etc, can also be used. It should be noted that the catalyst is added primarily to increase the rate of the reaction, and if desired the reaction can be conducted in the absence of the catalyst. The catalyst concentration can be between 0.001 to 1% by wt., however the preferred concentration is between 0.1% and 0.2% by wt.

The polyisocyanates useful in the synthesis of FOX polyurethanes are: hexamethylene diisocyanate (HDI), Isopherone diisocyanate (IPDI), Methylene diphenylisocyanate (MDI), saturated MDI (Des-W), polymeric MDI (Isonates), toulene diisocyanate (TDI), polymeric HDI (N-100 and N-3200), cyclohexylene-1,4-diisocyanate, and 2,2,4-trimethylhexmethylene diisocyanate. The NCO:OH ratio can be from 1.1 to 0.9, however the preferred ratio is 1.02.

Bulk materials are prepared by casting the above formulation in a mold, degassing the mixture, and then curing it at 65° C. for 16 to 36 h. A thin film is prepared by diluting the above formulation with THF, spreading the mixture over the substrate with a Doctor's blade, and then curing the coated substrate in an oven at 65° C. Alternately, the substrate can be dip-coated or spray coated and cured in an oven at 65° C.

The cure temperature can be between 20° C. to 150° C. The preferred temperature is 65° C. The above formulation can be cured at room temperature by increasing the amount of catalyst to ca. 0.5%. The cure is also dependent on the thickness of the sample and type of crosslinking agent. Thin samples cure within 3 h at 65° C., whereas ⅛ inch thick sample take between 8–16 h to cure. Also, amine-based crosslinking agents promote faster cures than polyols.

The mechanical properties of an unfilled elastomer are shown in Table 3. These properties indicate that polyurethanes prepared from FOX prepolymers are true elastomers (i.e., >100% recoverable elongation).

TABLE 3

| No. | Prepolymer | % F | Contact Angle | Tensile Modulus | Strain | Stress | Water Abs. |
|---|---|---|---|---|---|---|---|
| 1 | Poly 3-Fox | 31 | 110° | 79 | 926% | 670 | — |
| 2 | Poly 3/7-FOX (25:75) | 43 | 114° | 34 | 1,256 | 427 | 0.22% |
| 3 | Poly 7-FOX | 47 | 119° | 41 | 1,308 | 622 | 0.16% |
| 4 | Poly 3/15-FOX (25:75) | 52 | 128° | 67 | 1,117 | 344 | 0.18% |
| 5 | Teflon | 76 | 112° | — | — | — | — |

The effect of a filler on mechanical properties is demonstrated in Table 4.

TABLE 4

| | FILLER | | Contact | MECHANICAL | | |
|---|---|---|---|---|---|---|
| No | Type | % | Angle | T. Mod | Strain | Stress |
| 1* | — | 0 | 114° | 34 psi | 1,256% | 427 psi |
| 2 | Teflon | 5 | — | 41 psi | 1,616% | 556 psi |
| 3 | Teflon | 10 | — | 53 psi | 1,294% | 500 psi |
| 4 | Teflon | 20 | — | 73 psi | 1,226% | 425 psi |
| 5 | Carbon Black | 0.25 | 108° | 42 psi | 1,605% | 444 psi |

*Base polymer: Polyurethane from 25:75 Poly 3/7-FOX

As expected, the tensile modulus increases and % elongation decreases with increasing filler loading. It is noteworthy that the use of a low energy filler like Teflon does not degrade the mechanical properties of FOX polyurethane elastomers. This indicates that FOX polyurethanes will wet Teflon and thus allow Teflon to disperse, rather than agglomerate, in the filled polymer.

Surprisingly, FOX polyurethanes exhibit good adhesion to a variety of substrates such as stainless steel, aluminum, graphite, EPDM rubber, glass and wood. In a typical process, the substrate is coated with the polyurethane formulation, placed in an oven, and cured. Please note that no special treatment or primer is required to bond fluorinated polyurethane to the substrate. Peel strength indicates the bonding characteristics of the coating to substrate and is measured with an Instron. Polyurethanes from hydroxy-terminated polybutadiene bond strongly to EPDM substrates and exhibit peel strengths that are in the neighborhood of 9.5 lbs/in; the bond failure is cohesive. The polyurethane prepared from FOX-7 prepolymer, Isonol-93, and Des-W exhibit a peel strength of 9.5 lbs/in and an adhesive bond failure. The good bonding characteristics of FOX polyurethanes is attributed to the presence of polar urethane groups in the polymer backbone, which in contrast to fluoroalkyl groups, orient towards the high energy surface. A well adhering coating should, therefore, contain chemical groups that will contribute to enhance the polarity of the coating and bring it into the range of the substrate. A system containing both dipole-dipole and hydrogen-bond contributions is preferred over a system containing only one such contribution because of its broader compatibility. During application, the system must be sufficiently fluid in order to encourage rapid spreading, uniform coating and good wetting. Since Teflon has the fluorine symmetrically bonded to the polymer backbone, there is no dipole or hydrogen bonding with which the polymer may bond to a substrate surface. Consequently, a Teflon coating will not exhibit good adhesion or peel strength with its underlying substrate.

Thermal stability of FOX polyurethanes was determined by thermogravimetric analysis (TGA). These materials exhibit 0% wt. loss in air to 260° C. and onset of major thermal degradation in air at 275° C. This study indicates that FOX polyurethanes should not be exposed to temperatures in excess of 250° C.

The above results indicate that the polyurethanes prepared from FOX prepolymers are more hydrophobic and non-stick than Teflon. In sharp contrast to Teflon, FOX polyurethanes are tough elastomers that can be processed into thin coatings or into bulk articles. Moreover, these materials are flexible at low temperatures and can be used at temperatures as low as −50° C. Also, these materials can be bonded to a variety of substrates, and can be used between the temperature limits of −50° C. and 250° C. This invention provides novel materials that can be bonded strongly to a variety of substrates and at the same time provide a surface that is more hydrophobic and non-stick than Teflon. Materials with combinations of these properties are not known and thus FOX polyurethanes fulfill an important niche in the market place for processable, low surface energy elastomers.

Polyurethanes from FOX/THF Co-prepolymers

FOX/THF co-prepolymers may be also used to produce polyurethane elastomers with useful properties. Polyurethanes prepared from FOX/THF co-prepolymers exhibit better adhesion, higher abrasion resistance, and superior mechanical properties than those derived from FOX homo-prepolymers. Moreover, the key properties of FOX polyurethanes are not affected by incorporation of THF in the polymer structure. That is, polyurethanes prepared from FOX/THF co-prepolymers still exhibit low glass transition temperature, low coefficient of friction, and low surface energy—properties that are similar to those of polyurethanes derived from FOX homo-prepolymers.

The FOX/THF co-prepolymers described in this invention are difunctional and have terminal hydroxy groups. These hydroxy groups are primary and react readily with isocyanates to form high molecular weight polyurethane elastomers. In a typical reaction, the co-prepolymer is reacted with an equivalent amount of polyisocyanate in the presence of a catalyst and a crosslinking agent to form a 3-dimensional polymer network. If the functionality of the polyisocyanate is 2, then a crosslinking agent is needed to form a crosslinked network. However, if the functionality of the polyisocyanate is >2, then no crosslinking agent is needed. In some cases, additional crosslinking agent is added to improve the chemical and abrasion resistance of the polymer. The crosslinking agent normally used is a low molecular weight polyol or polyamine such as trimethylolpropane, Isonol 93, Jeffamines, trimethylolethane, pentarerythitol, triethanol-amine, diethanolamine, 4,4-methylene dianiline, MOCA, 1,4-butanediamine, diethylenetriamine, xylene diamine, etc. The preferred crosslinking agents are Isonol 93, trimethylolpropane and Jeffamines. The preferred catalyst is dibutyltin dilaurate, however other catalysts such as triethylamine, DABCO, Ferric acetylacetonate, triphenyl bismuth, tin octanoate, lead octanoate, etc., can also be used. The catalyst concentration is normally between 0.1 and 0.2% by weight. The polyisocyanates useful in the synthesis of fluorinated polyurethanes are hexamethylene diisocyanate (HDI), Isopherone diisocyanate (IPDI), 4,4-methylene diphenylisocyanate (MDI), polymeric MDI (Isonates), toluene diisocyanates, saturated MDI (HMDI), polymeric HDI (N-100 and N-3200), and trimethylhexane diisocyanate. The NCO:OH ratio can be from 1.1 to 0.9, but the preferred ratio is 1.02. Bulk materials are prepared by casting the above formulation in a mold, degassing the mixture under reduced pressure for 15 mins, and then curing it in an oven at 65° C. for 16 h. If a thin film is desired, a solvent, like THF, is added to reduce the viscosity, and the mixture is spread over the substrate with a doctor's blade to form a film of desired thickness. Alternately, the substrate can be dip-coated or spray coated, then cured in an oven at 60° C.–65° C.

Cure, that is the reaction of prepolymers with polyisocyanates and crosslinking agents to form high molecular weight, crosslinked polymer network, is normally conducted at temperatures from 20° C. to 150° C. The preferred cure temperature is 65° C. The above formulations can be cured at room temperature by increasing the amount of catalyst to 0.5%. Also, thin films cure faster than bulk materials. The cure time is also dependent on the amount of the catalyst, temperature, and the type of crosslinking agent. Higher catalyst loading and higher temperature favor faster cures. Also, amine-based cross-linking agents promote faster cures than polyols. A formulation containing FOX/THF co-prepolymer, Isonol-93, HMDI, and 0.2% wt. catalyst cures in ca. 7 h at 65° C. to give a tack free, ⅛ inch thick polyurethane elastomer. Under similar conditions, a 20 mil thick film will cure in 2 h at 65° C. When the above cure is repeated with an amine crosslinking agent, the cure time is reduced to <30 mins at 40° C.

In general, polyurethanes prepared from FOX/THF co-prepolymers are tack-free, opaque elastomers. They exhibit glass transition temperatures between −41° C. and −46° C., and static contact angles with water between 108° and 126°. These materials are insoluble in common organic solvents like methanol, toluene, hexanes, carbon tetrachloride, methyl ethylketone and kerosene, but swell in THF and Freon 113. The mechanical properties of an unfilled elastomer, as measured with an Instron, fall within the following limits:

| | |
|---|---|
| Tensile Modulus | 35 psi to 205 psi |
| Elongation at Break | 400% to 1624% |
| Tensile Strength | 380 psi to 624 psi |

An elastomer that has been characterized in detail is prepared from 60:40 7-FOX/THF co-prepolymer, Isonol 93 and HMDI, in the presence of dibutyltin dilaurate catalyst. The candidate material, a 3×5×0.2 inch$^3$ sample, is an opaque elastomer. The static contact angle of this material with doubly distilled water is 117°. By comparison, static contact angles of water with Teflon and 7-FOX polyurethane are 110° and 119°, respectively. The surface energy of the candidate material, as determined by the method of Wu et al., is 13.5 erg/cm$^2$. This value is considerably lower than that of Teflon (18.5 ergs/cm$^2$), but similar to that of 7-FOX polyurethane (13.2 ergs/cm$^2$). The above results indicates that polyurethane prepared from 7 -FOX/THF co-prepolymer is comparable in release characteristics and hydrophobicity to 7-FOX polyurethane, but is substantially more non-wettable and non-stick than Teflon. In view of the reduced amount of fluorinated starting materials required to assemble the mono-substituted FOX monomers of this invention and further in view of the reduced amount of FOX monomer required in order to assemble a FOX/THF co-prepolymer, there is a significant cost savings over pre-polymers assembled from the bis-substituted monomers or prepolymers assembled solely from the FOX monomers.

The candidate material exhibits a tensile modulus of 53 psi, elongation at break of 1624%, and a tensile strength of 624 psi. Recoverable elongation is in the neighborhood of 1200%. By comparison the mechanical properties of 7-FOX polyurethane are: tensile modulus=41 psi; elongation at break=1308%; and tensile strength=622 psi. This result is particularly interesting since it indicates that copolymerization of 7-FOX with THF improves both stress and strain capabilities of the 7-FOX polyurethane elastomer. It should be noted that the mechanical properties can be tailored by varying factors such as, crosslink density, type of isocyanate, amount of plasticizer, filler loading, % hard block, etc. The glass transition temperature of the elastomer, as measured with DSC, was −43° C., whereas by rheometric mechanical spectrometer (RMS) it is −42° C.

The candidate material exhibits good to excellent adhesion to a variety of substrates such as, stainless steel (SS 304), graphite, EPDM rubber, aluminum, and glass. Typically, the substrate is cleaned with water and acetone and then dried in an oven prior to use. Bonding is achieved by curing the mixture of prepolymer, crosslinking agent, polyisocyanate, and the catalyst directly on the substrate.

In one experiment, EPDM substrate was coated with a 0.20 inch thick film of the candidate material, and peel strength was measured with an Instron. The candidate material exhibited a peel strength of >10 lb/in with a cohesive bond failure. The peel strength of 7-FOX/THF polyurethane compares favorably with the peel strength of polyurethane prepared from hydroxy-terminated polybutadiene, Isonol 93 and HMDI (>9.8 lb/in, cohesive failure). The peel strength of 7-FOX polyurethane on EPDM rubber was 9.5 lbs and the failure was adhesive. Ideally, high peel strength characterized by cohesive failure is desired (i.e., the material will tear before delaminating from the substrate).

The coefficient of dynamic friction is approximately 0.33 for 7-FOX/THF polyurethanes and 0.31 for 7-FOX polyurethanes. By comparison, the coefficient of dynamic friction for a typical non-fluorinated polyurethane coating containing silicon oil is approximately 0.95.

The above results indicate that the copolymerization of FOX monomers with THF not only reduces the cost of manufacturing fluorinated prepolymers, but also provides material with superior properties. Moreover, FOX/THF polyurethanes exhibit better adhesion and superior mechanical properties than FOX polyurethanes, while retaining the key properties of FOX polyurethanes such as low glass transition temperature, high adhesion, processibility, high hydrophobicity, low coefficient of friction, and low surface energy.

Due to their unique combination of properties, polyurethanes prepared from FOX/THF co-prepolymers are useful as: fouling release coatings; abrasion resistant, low friction coatings for glass run window channels, belts and windshield wipers; bushing, gaskets, and engine mounts; encapsulants for electronic devices; binders for propellants and flares; artificial joints; dental materials; and coatings for automotive, marine and industrial applications. The preferred applications are fouling release coatings, coatings for window channels, and binders for propellants and flares.

DETAILED DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

A. Pre-monomer
   Experimental Section

The following examples detail the two step synthesis process of the mono-substituted premonomer. The synthesis of the intermediate dibromoacetate is detailed in Example 1. Example 2 and 3 detail the synthesis of the 3-bromomethyl-3-methyloxetane premonomer and the arylsulfonate of 3-hydroxymethyl-3-methyloxetane premonomer respectively. $^1H/^{13}C$ NMR analysis was performed on a Bruker MSL-300 spectrometer at 300 MHz in $CDCl_3$ solution with proton and carbon shifts in ppm relative to tetramethylsilane. IR analysis was performed on a Nicolet SX-5 spectrometer.

EXAMPLE A1

Preparation of 3-bromo-2-bromomethyl-2-methylpropyl Acetate

In a 12 L flask equipped with an overhead stirrer, reflux condenser, and addition funnel was placed 1,1,1-tris (hydroxymethyl)ethane (TME, 1.000 Kg, 8.32 mol) and glacial acetic acid (3.750 L). The mixture was allowed to stir until partial dissolution of the TME had occurred and then the sodium bromide (2.568 Kg, 24.96 mol) was added with vigorous stirring. The sulfuric acid (1.718 Kg, 16.64 mol) was then slowly added over 6 hours. After the addition was complete, the reaction mixture was heated to 120° C. for 48 hours. At this time GC evidence indicated that the reaction was complete and the mixture was cooled to room temperature and quenched with 7 L of ice water. The organic and aqueous phases were separated and the organic was washed with water, 0.5N NaOH (until neutral pH), brine, and then dried over $MgSO_4$ to yield the product as a clear colorless oil in 92% yield (2.206 Kg): IR (KBr) 2980–2800, 1744, 1374, 1242, 1043, 710 cm$^{-1}$; $^1$H NMR δ 1.20 (s, 3H), 2.11 (s, 3H), 3.48 (s, 4H), 4.09 (s, 2H); $^{13}$C NMR δ 20.12, 20.58, 38,21, 39.04, 67.08, 170.32.

EXAMPLE A2

Preparation of BrMMO Pre-monomer 3-Bromomethyl-3-methyloxetane

In a 50 L flask equipped with an overhead stirrer and reflux condenser was placed 3-bromo-2-bromomethyl-2-methylpropyl acetate (2.206 Kg, 7.66 mol), 3M NaOH (7.67 L, 22.98 mol), tetrabutylammonium bromide (123.47 g, 0.383 mol), and $CCl_4$ (7.66 L). The resulting heterogeneous solution was then refluxed at 70° C. overnight. At this time GC evidence indicated that the reaction was complete. The reaction was then cooled to room temperature. The organic and aqueous phases were separated, the organic phase was washed with water and brine, and then dried over $MgSO_4$.

Removal of the solvent gave the product as a clear, light yellow oil (1.224 Kg) in 97% yield. Distillation gave a clear, colorless oil (1.189 Kg) in 94% yield, bp 46° C./0.3 mm Hg; IR (KBr) 2980–2800, 1242, 1201, 1147, 704 cm$^{-1}$; $^1$H NMR δ 1.44 (s, 3H), 3.65 (s, 2H), 4.40 (d, J=5.8 Hz, 2H), 4.45 (d, J=5.8 Hz, 2H) $^{13}$C NMR 22.38, 40.58, 41.29, 80.54.

Example A3

Preparation of Pre-monomer p-Toluenesulfonate of 3-Hydroxymethyl-3-methyloxetane A solution of 3-Hydroxymethyl-3-methyloxetane (612 g, 6 mol) in pyridine (800 ml) was cooled to −10° C. and treated, slowly, with a solution of p-toluenesufonyl chloride (1364 g, 7 mol) in pyridine (700 ml). The rate of addition was maintained so that the contents of the flask were kept below −5 ° C. Upon complete addition, the solution temperature was held at −5° C. for 30 minutes and then at room temperature for 2 hours. The contents of the flask were quenched by pouring it into ice water (10 L), and the precipitated solid was filtered, washed with water and dried in air. The purity of the product as determined by GLC analysis was >98%. By this method, 1352 g of the desired product was obtained, representing an 88% yield.

The yield and purity of the bromomethyl and arylsulfonate premonomer product are extremely high and these examples clearly show how easily and inexpensively the mono-substituted premonomer of this invention is synthesized.

B. Monomer/Prepolymer Examples

Experimental

In the following examples, the polymerization was practiced with boron trifluoride etherate catalyst, although the currently preferred catalyst is boron trifluoride tetrahydrofuranate. Commercially available boron trifluoride etherate and boron trifluoride tetrahydrofuranate were distilled under reduced pressure prior to use. Similarly, the initiator, 1,4-butanediol, was purchased commercially and distilled from calcium hydride and stored over a 4 Å molecular sieve prior to use.

The polymerization was conducted in jacketed glass reactors equipped with a mechanical stirrer reflux condenser and a digital thermometer. $^1$H, $^{13}$C and $^{19}$F NMR analysis were conducted on a Bruker MSL-300 spectrometer in deutrochloroform solution with proton and carbon chemical shifts reported in parts per million (ppm) relative to tetramethylsilane and fluorine shifts relative to trichlorofluoromethane. Infrared analysis was conducted on a Nicolet SX-5 spectrometer. Gel permeation chromatography (GPC) was conducted on a Waters gel permeation chromatograph equipped with four ultrastyragel columns (100 Å, 500 Å, 10$^3$ Å and 10$^4$ Å) a differential refractive index detector and a Data Module 730. THF was used as the mobile phase. The GPC was calibrated with a series of well characterized (i.e., $M_n$, $M_w$ are well known) polystyrene standards (Narrow Standards), and thus the number average molecular weight ($M_n$) and weight average molecular weight ($M_w$) reported are expressed relative to styrene. Differential scanning calorimetry (DSC) was performed on a DuPont 990 thermal analyzer system at a heating rate of 10° C./min. Elemental analysis was conducted by Galbraith Laboratories in Knoxville, Tenn. Inherent viscosity of prepolymers was measured in THF at a concentration of 0.5 g/dL at 25° C. Equivalent weights were determined by $^1$H NMR employing trifluoroacetic anhydride (TFAA) end group analysis. Fluoroalcohols were purchased commercially from either 3M Corporation or DuPont Corporation, and, with the exception of DuPont's Zonyl BA-L alcohols, were used as received. Purification of the Zonyl BA-L alcohols is described in Example B6.

In Examples B1 and B2 we clearly establish proof of the reaction mechanism for the production of the fluorinated alkoxymethylene-3-methyloxetane monomer using the arylsulfonate premonomer.

EXAMPLE B1

Preparation of 3-FOX Monomer 3-(2,2,2-Trifluoroethoxymethyl)-3-methyloxetane

Synthesis of the 3-FOX oxetane monomer is performed as follows:

A dispersion of 50 weight percent (2.8 grams, 58.3 mmol) sodium hydride in mineral oil, was washed twice with hexanes and suspended in 35 milliliters of dimethyl formamide. Then, 5.2 grams (52 mmol) of trifluoroethanol was added and the mixture was stirred for 45 minutes. A solution of 10.0 grams (39 mmol) of 3-hydroxymethyl-3-methyloxetane p-toluenesulfonate in 15 milliliters of dimethyl formamide was added and the mixture was heated at 75°–85° C. for 20 hours, when $^1$H MNR analysis of an aliquot sample showed that the starting sulfonate had been consumed.

The mixture was poured into 100 milliliters of ice water and extracted with 2 volumes of methylene chloride. The combined organic extracts were washed twice with water, twice with 2 weight percent aqueous hydrochloric acid, brine, dried over magnesium sulfate, and evaporated to give 6.5 grams of 3-(2,2,2-trifluoroethoxymethyl)-3-methyloxetane as an oil containing less than 1 weight percent dimethyl formamide. The yield of this product was 90 percent. The oil was distilled at 30° C. and 0.2 millimeters mercury pressure to give 4.3 grams of analytically pure 3-FOX, corresponding to a 60 percent yield. The analyses of the product were as follows: IR (KBr) 2960–2880, 1360–1080, 990, 840 cm$^{-1}$; $^1$H NMR δ 1.33 (s, 3H), 3.65 (s,2H), 3.86 (q, J=8.8 Hz, 2 H), 4.35 (d, J=5.6 Hz, 2 H), 4.51 (d, J=5.6 Hz, 2 H); $^{13}$C NMR δ 20.72, 39.74, 68.38 (q, J=40 Hz), 77.63, 79.41, 124 (q, J=272 Hz). The calculated elemental analysis for $C_7H_{11}F_3O_2$ is: C=45.65; H=6.02; F=30.95. The experimental analysis found: C=45.28; H=5.83; F=30.59.

EXAMPLE B2

Preparation of 7-FOX Monomer 3-(2,2,3,3,4,4,4-Heptafluorobutoxymethyl)-3-methyloxetane A 50 weight percent dispersion of sodium hydride (6.1 grams, 127 mmol) in mineral oil, was washed twice with hexanes and was suspended in 60 milliliters of dimethyl formamide. Then 24.0 grams (120 mmol) of 2,2,3,3,4,4,4-heptafluorobutan-1-ol was added and the mixture was stirred for 45 minutes. A solution of 25.0 grams (97.5 mmol) of 3-hydroxymethyl-3-methyloxetane p-toluenesulfonate in 15 milliliters of dimethyl formamide was added and the mixture was heated at 75°–85° C. for 30 hours when $^1$HNMR analysis of an aliquot showed that the starting sulfonate had been consumed.

The mixture was poured into 100 milliliters of ice/water and extracted with two volumes of methylene chloride. The combined organic extracts were washed twice with water, twice with 2 weight percent aqueous hydrochloric acid, brine, dried over magnesium sulfate, and evaporated to give 27.5 grams of 3-(2,2,3,3,4,4,4-heptafluorobutoxymethyl)-3-methyloxetane (i.e., 7-FOX) as an oil. The oil was distilled at 33° C. and 0.2 millimeters mercury pressure to give 12.2 grams of analytically pure ether, corresponding to a 44 percent yield. The experimental analyses were: IR (KBr) 2960–2880, 1280–1030, 995, 840 cm$^{-1}$, $^1$H δ NMR 1.31 (s, 3 H), 3.67 (s 2 H), 3.99 (t, J=13.3 Hz, 2 H), 4.34 (d, J=5.7 Hz 2 H), 4.50 (d, J=5.7 Hz, 2 H); $^{13}$C NMR δ 20.242, 39.627, 67.778, 77.730, 79.110, 108.72, 114.7, 117.58; $^{19}$F NMR δ −81.4, −120.6, −128.1. The calculated elemental analysis for $C_9H_{11}F_7O_2$ is C=38.04; H=3.90; F=46.80. The experimental analyses found: C=38.03; H=3.65; and F=46.59.

Examples B3, B4 and B5 provide detail of the reaction mechanism for the synthesis of the 15-FOX, 13-FOX and a mixture of 13/17/21-FOX using the 3-chloromethyl-3-methyloxetane, the 3-bromomethyl-3-methyloxetane and the 3-iodomethyl-3-methyloxetanes as the premonomers, respectively. Note that although the perfluoroalkyl moiety on the side-chain increases in size, the substitution of the fluorinated alkoxide for the halogen proceeds and the yields are high. Further, we have clearly shown by way of Example B5 that a mixture of perfluorinated alkoxymethylene-3-methyloxetanes may be produced by merely introducing a mixture of fluorinated alcohols.

We also show that this reaction works for those fluorinated alcohols in which the fluoroalkyl is separated from the hydroxy group by 2 methylenes as well as by 1 methylene group (i.e., the process is equally effective for the DuPont alcohols as it is for the 3M alcohols).

EXAMPLE B3

Preparation of 15-FOX 3-(2,2,3,3,4,4,5,5,6,6,7,7,8,8,8-Pentadecafluorooctyloxymethyl)-3-methyloxetane A dispersion of 50 weight percent sodium hydride (4.0 g, 83 mmol) in mineral oil was washed with hexanes and suspended in 200 milliliters of dimethylformamide. A solution of 30 grams of 2,2,3,3,4,4,5,5,6,6,7,7,8,8,8-pentadecafluorooctan-1-ol (75 mmol) in 50 milliliters of dimethylformamide was added over a period of 3 hours, and the resulting mixture was stirred at room temperature for one hour. Next, a solution of 9.3 grams (77 mmol) of 3-chloromethyl-3-methyloxetane in 20 milliliters of dimethylformamide was added and the resulting mixture was heated at 75° C. for 16 hours. The mixture was cooled to room temperature and slowly poured into 1 liter of ice/water and extracted with two volumes of Freon 113. The combined organic extracts were washed twice with water, once with 2 weight percent aqueous hydrochloric acid and once with brine, dried over magnesium sulfate, filtered, and evaporated to give 32 grams of crude product. The crude product was distilled under reduced pressure to give 26.5 grams (73%) of analytically pure 3-(2,2,3,3,4,4,5,5,6,6,7,7,8,8,8-pentadecafluorooctoxymethy)-3-methyloxetane (i.e., 15-FOX), an oil with a boiling point of 68° to 70° C./1.6mm-Hg. The experimental analyses were: $^1$H NMR (CDCl$_3$/Freon 113) δ 4.49 and 4.37 (AB, J=5.5 Hz, 4 H), 4.00 (triplet, J=13.2 Hz, 2 H), 3.70 (singlet, 2 H), and 1.32 (singlet, 3 H); $^{13}$C NMR δ 21.02, 40.33, 68.77 (triplet, J=146.2 Hz), 78.60, and 79.87 (signals from carbon bearing fluorine are not included due to complex splitting patterns and low peak intensities); $^{19}$F NMR δ −81.3 (3 F), −119.9 (2F), −122.6 (2 F), −123.3 (2 F), −123.5 (2 F), −123.9 (2 F) and −126.8 (2 F). The elemental analysis was: Calculated for $C_{13}H_{11}F_{15}O_2$: C, 32.2; H, 2.3; F, 58.9. Found: C, 32.2; H, 2.2; F, 58.3.

EXAMPLE B4

Preparation of 13-FOX 3-(3,3,4,4,5,5,6,6,7,7,8,8,8-Tridecafluorooctyloxymethyl)-3-methyloxetane In a manner similar to that described above, 12.0 grams of 3-bromomethyl-3-methyloxetane (73 mmol ) was reacted with 26.5 grams of 3,3,4,4,5,5,6,6,7,7,8,8,8-tridecafluorooctan-1-ol (72.7mmol) in 300 milliliters of dimethylformamide in the presence of 3.9 grams of a 50 weight percent dispersion of sodium hydride (81 mmol) in mineral oil at 85° C. for 24 hours to give 21.5 grams (70% yield) of 3-(3,3,4,4,5,5,6,6,7,7,8,8,8-tridecafluorooctyloxymethyl)-3-methyloxetane, a colorless oil with a boiling point of 66°–68° C./2–2.5 mm-Hg; $^1$H NMR (CDCl$_3$) δ 4.50 and 4.36 (AB, J=5.5 Hz, 4 H), 3.78 (t, J=6.6 Hz, 2 H), 3.53 (s, 2 H), 2.42 (triplet of triplets, J=6.6 and 18 Hz, 2 H), and 1.31 (s, 3 H); $^{13}$C NMR (CDCl$_3$) δ 79.89, 78.30, 63.31, 39.9, 31.64 (t), and 21.1 (signals due to carbons bearing fluorines are not included due to the complex splitting patterns and low peak intensities); $^{19}$F NMR δ −81.4 (3 F), −113.8 (2 F), −118.2 (2 F), −112.3 (2 F), −124.1 (2 F) and −126.7 (2 F). The elemental analysis was: Calculated for $C_{13}H_{13}F_{13}O_2$: C, 34.8; H, 2.9; F, 55.1. Found: C, 35.1; H, 3.0; F, 54.7.

Note that the fluorinated alcohols in Examples B4 and B6 were supplied by DuPont (i.e., $R_f$—$CH_2CH_2OH$). These alcohols are inexpensive and available in bulk, however, they are not pure and must be purified prior to use in these reactions. Example B5 details how these fluoroalcohols may be purified. On the other hand, the fluoroalcohols of Examples B1, B2 and B3 have a methanol group pendant to the perfluoroalkyl moiety (i.e., $R_f$—$CH_2OH$) and are purchased From 3M Corporation as reagent grade, not requiring further purification.

EXAMPLE B5

Purification of Commercial Fluoroalcohols

Zonyl BA-L is a narrow distribution, oligomeric mixture of fluoroalcohols that is available from Dupont Chemicals in pilot plant quantities. Zonyl BA-L is a yellow liquid which by GLC is a mixture of the following oligomers: 3-(3,3,4,4,5,5,6,6,7,7,8,8,8-tridecafluorooctan-1-ol (C8, 60%); 3,3,4,4,5,5,6,6,7,7,8,8,9,9,10,10,10-heptadecafluorodecan-1-ol (C10, 26%); 3,3,4,4,5,5,6,6,7,7,8,8,9,9,10,10,11,11,12,12,12-heneicosafluorododecanol (C12, 6%); and various unidentified high boiling compounds (8%). Zonyl BA-L was washed with equal volumes of 10 weight percent aqueous sodium thiosulfate, 10 weight percent aqueous sodium bicarbonate (to remove HF), water and brine, dried, filtered, and distilled under reduced pressure (3mm-Hg) at 50°–100° C. to give a mixture of 69% C8, 26% C10 and 5% C12 in 83% yield.

EXAMPLE B6

Preparation of a Mixture: 13/17/21-FOX 3,3,4,4,5,5,6,6,7,7,8,8-Tridecafluorooctyloxymethyl-, 3,3,4,4,5,5,6,6,7,7,8,8,9,9,10,10,10-Heptadecafluorodecyloxymethyl-, and 3,3,4,4,5,5,6,6,7,7,8,8,9,9,10,10,11,11,12,12,12-Heneicosafluorododecyloxymethyl-3-methyloxetane In a manner similar to that described above, a mixture of 69% C8, 26% C10 and 5% C12 fluoroalcohols (distilled Zonyl BA-L from Example B5, 51.6 grams, 129 mmol) was reacted with 27 grams of 3-iodomethyl-3-methyloxetane (127 mmol) in 500 milliliters of dimethylformamide at 85° C. for 18 hours to give 60 grams of crude product. The crude product was fractionally distilled through a 6" Vigerux column to yield the following fractions: Fraction #1 (4.8 grams) was collected between 25° C. and 45° C. at 3.5–2.9 mm-Hg, and was a mixture of unreacted fluoroalcohols. Fraction #2 (2.8 grams) was collected at 45°–71° C./0.7–3.0 mm-Hg, and was a mixture of unreacted fluoroalcohols and fluorinated oxetane monomers. The final fraction (49 grams, 80%), boiling at 70°–85° C./0.7–0.9 mm-Hg, was a mixture of 73% 3,3,4,4,5,5,6,6,7,7,8,8,8-tridecafluorooctyloxymethyl-3-methyloxetane (13-FOX), 24% 3,3,4,4,5,5,6,6,7,7,8,8,9,9,10,10,10-heptadecafluorodecyloxymethyl-3-methyloxetane (17-FOX), and 3% 3,3,4,4,5,5,6,6,7,7,8,8,9,9,10,10,11,11,12,12,12-heneicosafluorododecyloxymethyl-3-methyloxetane (21-FOX), a colorless oil with a boiling point of 70°–85° C./0.7–0.9 mm-Hg; $^1$H NMR (CDCl$_3$) δ 4.50 and 4.35 (AB, J=5.9 Hz, 4 H), 3.78 (t, J=6.6 Hz, 2 H), 3.53.(s, 2 H), 2.42 (tt, J=6.6 and 17.6 Hz, 2 H), and 1.31 (s, 3 H); $^{13}$C NMR δ 21.3, 31.86 (t, J=130.1 Hz), 40.2, 63.6, 76.8, and 80.2 (signals for carbons bearing fluorine are not included due to complex splitting patterns and overlap of signals; $^{19}$F NMR δ −81.5, −113.8, −122.3, −123.3, −124.1, −124.5, −125.8, and 126.7.

Phase Transfer Catalyst Process

Examples B7 and B8 provide details as to the preferred process for synthesizing the FOX monomers of this invention using a phase transfer catalyst (PTC).

EXAMPLE B7

Preparation of 7-FOX Using PTC Process 3-(2, 2, 3, 3, 4, 4, 4-Heptafluorobutoxymethyl)-3-Methyloxetane A 2 L, 3 necked round bottom flask fitted with a reflux condenser, a mechanical stirrer, a digital thermometer and an addition funnel was charged with 3-bromomethyl-3-methyloxetane (351.5 g, 2.13 mol), heptafluorobutan-1-ol (426.7 g, 2.13 mol), tetrabutylammonium bromide (34.4 g) and water (85 ml). The mixture was stirred and heated to 75° C. Next, a solution of potassium hydroxide (158 g, 87% pure, 2.45 mol) in water (200 ml) was added and the mixture was stirred vigorously at 80°–85° C. for 4 hours. The progress of the reaction was monitored by GLC and when GLC analysis revealed that the starting materials were consumed, the heat was removed and the mixture was cooled to room temperature. The reaction mixture was diluted with water and the organic layer was separated and washed with water, dried and filtered to give 566 g (94%) of crude product. The crude product was transferred to a distillation flask fitted with a 6 inch column and distilled as follows:

Fraction #1, boiling between 20° C.–23° C./10mm-Hg, was found to be a mixture of heptafluorobutanol and other low boiling impurities, was discarded;

Fraction #2, boiling between 23° C. and 75° C./1 mm-Hg, was found to be a mixture of heptafluorobutanol and 7-FOX, was also discarded; and Fraction #3, boiling at 75° C./1 mm-Hg was >99% pure 7-FOX representing an overall yield of 80.2%

NMR and GLC data revealed that 7-FOX produced by this method was identical to 7-FOX prepared using the sodium hydride/DMF process.

EXAMPLE B8

Preparation of 15-FOX Using PTC Process 3-(2, 2, 3, 3, 4, 4, 5, 5, 6, 6, 7, 7, 8, 8, 8-Pentadecafluorooctyloxymethyl)-3-methyloxetane In a manner similar to the that of Example B14, a mixture of 3-bromomethyl-3-methyloxetane (468 g, 2.84 mol), 2,2,3,3,4,4,5,5,6,6,7,7,8,8,8-pentadecafluorooctan-1-ol (1032 g, 2.58 mol), tetrabutylammonium bromide (41.5 g), potassium hydroxide (208 g, 3.23 mol), and water (1680 ml) was heated under reflux for 3 hours. GLC analysis revealed complete consumption of starting materials. The reaction mixture was diluted with water, worked-up in the usual manner, and distilled under reduced pressure to give 1,085 g of 15-FOX, representing an overall yield of 87%; bp 82° C./0.1 mm-Hg. The distilled material was >99% pure as indicated by GLC and was used in subsequent polymerization reactions.

The first of three Comparative Examples below show that we are able to easily synthesize, using the process of our invention, in high yield, the bis-equivalent to our 3-FOX monomer.

In the second Comparative Example we show that we can easily homopolymerize, using the process of our invention, the bis 3-FOX to produce the bis 3-FOX prepolymer. As expected and consistent with the technology of Falk et al., the bis-prepolymer of this Comparative Example was a white waxy crystalline solid, unlike the low viscosity oils of the prepolymers of this invention. This is attributable to the ordered structure of the fluoroalkoxy side-chains resulting in efficient packing of the prepolymers into a crystalline structure.

In the third Comparative Example we show that a bis-monomer having much longer fluoroalkoxy side-chains may still be homopolymerized by the process of this invention. In other words, the homopolymerization of the bis-monomer is not limited by the size of the fluoroalkoxy groups. This is unexpected in view of the difficulties described in the background in achieving homopolymerization of the bis-substituted oxetanes. However, we observe that as the fluorinated side-chains of the bis-monomer become larger, homopolymerization results in a much higher fraction of the undesirable, non-functional cyclic tetramer. In our third Comparative Example the initial fraction of the cyclic tetramer byproduct is 32%. Even after further purification, the cyclic tetramer was still present at 9%. It is hypothesized that the presence of the cyclic tetramer impurity resulted in the prepolymer being a liquid rather than the expected solid, as it is well known that impurities will prevent crystallization. Increasing the size of the fluorinated side-chains results in increasing yields of the cyclic tetramer impurity and lower yields of the prepolymer. This suggest that the homopolymerization of the bis-monomer, although possible by the process of this invention, may not be commercially desirable for those bis-monomers having larger side-chains. In comparison, the FOX prepolymers of this invention do not exhibit decreasing yields/quality with increasing side-chain length. Consequently, the FOX prepolymers of this invention make possible the economic production of fluorinated polyurethanes having outstanding surface properties (see Exhibit 1).

COMPARATIVE EXAMPLE B9-a

Preparation of Bis-3-FOX 3,3-Bis-(2,2,2-trifluoroethoxymethyl)oxetane

A 50 weight percent dispersion of sodium hydride in 18.4 grams (0.383 mol) of mineral oil, was washed twice with hexanes and was suspended in 200 milliliters of dimethyl formamide. Then, 38.3 grams (0.383 mol) trifluoroethanol was added dropwise over 45 minutes while hydrogen gas evolved. The mixture was stirred for 30 minutes and a solution of 30.0 grams (0.073 mol) of 3,3-bis (hydroxymethyl)oxetane di-p-toluenesulfonate in 50 milliliters of dimethyl formamide was added. The mixture was heated to 75° C. for 64 hours when $^1$H NMR analysis of an aliquot showed that the starting sulfonate had been consumed.

The mixture was poured into water and extracted with two volumes of methylene chloride. The combined organic extracts were washed with brine, 2 weight percent aqueous hydrochloric acid, water, dried over magnesium sulfate, and evaporated to give 17.5 grams of 3,3-bis(2,2,2-trifluoroethoxymethyl)oxetane as an oil containing less than 1 weight percent dimethyl formamide. The oil was purified by bulb-to-bulb distillation at 42°–48° C. and 10.1 millimeters mercury pressure to give 15.6 grams of analytically pure bis-3-FOX, corresponding to a 79 percent yield. The analyses of the product were as follows: $^1$H NMR δ 3.87 (q, J=8.8 Hz, 4 H), 4.46 (s, 4 H); $^{13}$C NMR δ 43.69, 68.62 (q, J=35 Hz), 73.15, 75.59, 123.87 (q, J=275 Hz); $^{19}$F NMR δ –74.6 (s). The calculated elemental analysis for $C_9H_{12}F_6O_3$ is: C=38.31; H=4.29; and F=40.40. The experimental analyses found: C=38.30; H=4.30; and F=40.19.

COMPARATIVE EXAMPLE B9-b

Preparation of the Bis-3-FOX Prepolymer

Poly 3,3-bis(2,2,2-trifluoroethoxymethyl)oxetane

A solution of 33.9 milligrams (0.378 mmol) of butane-1,4-diol and 106.3 milligrams (0.75 mmol) of boron trifluoride etherate in 3.8 grams of methylene chloride was stirred at ambient temperature for 15 minutes under nitrogen in a dry polymerization flask. The solution was cooled to 1.5° C. and a solution of 1.88 grams (6.67 mmol) of 3,3-bis(2,2,2-trifluoroethoxymethyl)oxetane in 2.3 grams of methylene chloride was added. The resultant solution was stirred for 16 hours at 1°–2° C. at which time $^1$H NMR analysis of an aliquot indicated that the starting oxetane had been consumed.

The solution was warmed to ambient temperature and quenched with water. The organic layer was washed with brine, 2 percent aqueous hydrochloric acid, and evaporated to give 1.62 grams of poly 3,3-bis(2,2,2-trifluoroethoxymethyl)oxetane, corresponding to 85% yield. The prepolymer was a white, waxy solid. The polymer analyses were: DSC mp 80.96° C. (26.35 Joules/gram); GPC: $M_n$=5321, $M_w$=7804, polydispersity=1.47; inherent viscosity 0.080 dL/g; $^1$H NMR δ 1.60 (broad singlet), 3.36 (s, 4 H), 3.58 (s, 4 H), 3.79 (q, 4 H); $^{13}$C NMR 45.49, 68.25 (q, J=33 Hz), 69.20, 70.97, 123.81 (q, J=280 Hz).

COMPARATIVE EXAMPLE B9-c

Homopolymerization of Bis-Monomer 3,3-Bis(2,2,3,3,4,4,4-Heptafluorobutoxymethyl) Oxetane In a manner similar to that described in Example B7-b, a solution of 252 grams of 3,3-bis(2,2,3,3,4,4,4-heptafluorobutoxymethyl) oxetane (523 mmol) in 75 milliliters of Freon 113 was added to a mixture of 1.05 grams of boron trifluoride tetrahydrofuranate (7.5 mmol) and 0.265 gram of 1,4-butanediol (2.93 mmol) in 178 milliliters of methylene chloride at 10° C. The mixture was stirred at room temperature for 48 hours at which time NMR analysis of an aliquot indicated 96 percent conversion. The reaction was quenched with water and the polymer was precipitated into methanol to give, after drying at 80° C./2 mm-Hg for 16 hours, 211 grams of poly 3,3-bis (2,2,3,3,4,4,4-heptafluorobutoxymethyl) oxetane, a colorless oil in 84 percent yield. GPC analysis of this oil revealed it was a mixture of 68% linear and 32% cyclic materials. The cyclic product was isolated and identified as the cyclic tetramer, a white waxy solid with a melting point of 80° C.; $^1$H NMR δ 3.87 (t, J=13.5 Hz, 4 H), 3.54 (s, 4H), and 3.32 (S, 4H) (No end groups were observed on addition of trifluoroacetic anhydride); $^{13}$C NMR δ 71.2, 68.6, 68.4 (t), and 46.2 (signals due to carbons bearing fluorine are not included).

The above oil was further purified by first dissolving the material in methylene chloride/Freon 113 (75:25 mixture), precipitating the polymer into a 10 fold excess of methanol, stirring the precipitated oil with tetrahydrofuran at room temperature for 2 days, and finally separating and drying the insoluble fraction at 85° C. at 2 mm-Hg for 16 hours. This yielded 128 grams of a clear, viscous oil, corresponding to 51% overall yield. The oil by GPC analysis was determined to be a mixture of 91% linear polymer and 9% cyclic tetramer. The polymer analyses were: GPC: $M_n$=5,526, $M_w$=7,336, polydispersity=1.32; $^1$H NMR (CDCl$_3$/Freon 113/TFAA) δ 3.39 (s, 4 H), 3.59 (s, 4 H), 3.87 (t, J=13.5 Hz, 4 H) and 4.40 (s, —CH$_2$OCOCF$_3$); Equivalent Weight based on $^1$H NMR=2,600; $^{13}$C NMR (CDCl$_3$/Freon 113) δ 46.4, 68.5 (t), 70.1 and 72.1 (signals from carbons bearing fluorines are not included).

Examples B10 through B15 provide details on the polymerization of the FOX monomers to provide the FOX prepolymers of this invention.

Examples B10, B11 and B12 detail the homopolymerization of the 3-FOX, 7-FOX and 13-FOX respectively to provide random, asymmetrical prepolymers. Note that the yield of the 7-FOX prepolymer of Example B11 produced from the 7-FOX mono-substituted monomer resulted in a much higher yield of the prepolymer than that obtained from the bis-7-FOX homopolymerization of Comparative Example B9-c (83% versus 51%).

Example B12 uses the preferred BF3.THF catalyst.

EXAMPLE B10

Homopolymerization of 3-FOX 3-(2,2,2-Trifluoroethoxymethyl)-3-methyloxetane

A solution of 34.3 milligrams (0.38 mmol) of butane-1, 4-diol and 109.7 milligrams (0.77 mmol) of boron trifluoride etherate in 4 grams of methylene chloride was stirred at ambient temperature for 15 minutes under nitrogen in a dry polymerization flask. The solution was cooled to 1.5° C. and a solution of 1.20 grams (6.52 mmol) of 3-(2,2,2-trifluoroethoxymethyl)-3-methyloxetane in 1.3 grams of methylene chloride was added. The resultant solution was stirred for 5 hours at 1°–2° C. at which time $^1$H NMR analysis of an aliquot indicated that the starting oxetane had been consumed. The solution was warmed to ambient temperature and quenched with water. The organic layer was washed with brine, 2 weight percent aqueous hydrochloric acid, and evaporated to give 1.053 grams of poly-3-(2,2,2-trifluoroethoxymethyl)-3-methyloxetane as an oil, corresponding to a 88 percent yield. The polymer analyses were:

DSC Tg –45° C., decomposition temperature was greater than 200° C.; GPC $M_n$=7376, $M_w$=7951, polydispersity 1.08, inherent viscosity 0.080 dL/g; Equivalent Weight by $^1$H NMR=6300; $^1$H NMR δ 0.95 (s, 3 H), 3.26 (m, 4 H), 3.52 (s, 2 H) 3.84 (q, 2 H); $^{13}$C NMR δ 17.57, 42.09, 69.30 (q, J=33 Hz), 74.42, 75.90, 125.18 (q, J=280 Hz).

EXAMPLE B11

Homopolymerization of 7-FOX

Poly-3-(2,2,3,3,4,4,4-heptafluorobutoxymethyl)-3-methyloxetane

A solution of 34.7 milligrams (0.38 mmol) of butane-1,4-diol and 109.7 milligrams (0.77mmol) of boron trifluoride etherate in 3.4 grams of methylene chloride was stirred at ambient temperature for 15 minutes under nitrogen in a dry polymerization flask. The solution was cooled to 1.5° C. and a solution of 2.00 grams (7.08 mmol) of 3-(2,2,3,3,4,4,4-heptafluorobutoxymethyl)-3-methyloxetane (i.e., 7-FOX) in 3.3 grams of methylene chloride was added. The resultant solution was stirred for 4 hours at 1.2° C.; at which time $^1$H NMR analysis of an aliquot indicated that the starting oxetane had been consumed.

The solution was warmed to ambient temperature and quenched with water. The organic layer was washed with brine, 2 percent aqueous hydrochloric acid, and evaporated to give 1.65 grams of poly-3-(2,2,3,3,4,4,4-heptafluorobutoxymethyl)-3-methyloxetane, corresponding to a 83% yield. The prepolymer was an oil and had the following analyses: GPC $M_n$=4066, $M_w$=5439, polydispersity=1.34, inherent viscosity 0.054 dL/g.

This oil was further extracted with methanol and dried to give 1.46 grams of poly-7-FOX, corresponding to 72% yield, and has the following analyses: DSC: Tg=–45° C.; GPC: $M_n$=4417, $M_w$=5658, polydispersity=1.28; inherent viscosity=0.056 dL/g; Equivalent weight by $^1$H NMR=6359, $^1$H NMR δ 0.93 (s, 3 H), 3.24 (m, 4 H), 3.48 (s, 2 H), 3.92 (q, J=13.6 Hz, 2 H); $^{13}$C MMR 16.14, 40.57, 67.37 (t), 72.89, 74.76 (signals from carbon-bearing fluorie are not included).

EXAMPLE B12

Homopolymerization of 13-FOX 3-(3,3,4,4,5,5,6,6,7,7,8,8,8-Tridecafluorooctyloxymethyl)-3-methyloxetane In a manner similar to that described in Example B9, a solution of 10 grams of 3-(3,3,4,4,5,5,6,6,7,7,8,8,8-tridecafluorooctyloxymethyl)-3-methyloxetane (22.3 mmol) in three milliliters of Freon 113 was added dropwise to a mixture of 109 milligrams of boron trifluoride tetrahydrofuranate (0.78mmol) and 35 milligrams of 1,4-butanediol (0.39 mmol) in methylene chloride at 10° C. The mixture was stirred at room temperature for 24 hours, quenched with water, and precipitated in methanol to give, after drying at 80° C./2 mm-Hg for 16 hours, 8.3 gram of poly 3-(3,3,4,4,5,5,6,6,7,7,8,8,8-tridecafluorooctyloxymethyl)-3-methyloxetane, a clear colorless oil. The polymer analyses were: Inherent viscosity=0.067 dL/g; GPC: $M_n$=5,340, $M_w$=6,620, Poly Dispersity=1.24; DSC, Tg=–38° C.; $^1$H NMR (CDCl$_3$/Freon 113/trifluoroacetic anhydride (TFAA)) δ 3.67 (t, 5.9 Hz, 2 H), 3.31 (s, 2 H), 3.21 (m, 4 H), 2.35 (m, 2 H), and 0.93 (s, 3 H); $^1$H NMR (CDCl$_3$/Freon 113) 0.95 (s, 3 H), 2.37 (br t, J=18.3 Hz, 2 H), 3.25 (m, 4 H), 3.35 (s, 2H), 3.71 (t, 6.0 Hz, 2 H), and 4.30 (s, –C$\underline{H}_2$OCOCF$_3$); Equivalent Weight based on $^1$H NMR was 4,756, $^{13}$C NMR (CDCl$_3$/Freon 113) δ 17.35, 31.75, 41.5, 63.4, 74.1 and 74.3 (signals from carbon bearing fluorine are not included).

Examples B13–B15 provide details as to the copolymerization of various FOX monomers to provide FOX co-prepolymers. The polymerization in all three Examples is catalyzed with BF$_3$-THF. Noteworthy is the high yields in the 80%–85% in all three Examples.

EXAMPLE B13

Copolymerization of 3-FOX and 7-FOX 3-(2,2,2,-Trifluoroethoxymethyl)-3-methyloxetane with 3-(2,2,3,3,4,4,4-Heptafluorobutoxymethyl)-3-methyloxetane In a manner similar to that described in Example B9, a solution of 35 grams of 3-(2,2,2,-trifluoroethoxymethyl)-3-methyloxetane (190 mmol) and 183 grams of 3-(2,2,3,3,4,4,4-heptafluorobutoxymethyl)-3-methyloxetane (644mmol) in 50 milliliters of 1,1,2-trichlorotrifluoroethane was added to a mixture of 0.390 gram of 1,4-butanediol (4.33 mmol), 1.55 grams of boron trifluoride tetrahydrofuranate (11.1 mmol), and 100 milliliters of methylene chloride at 18° C. The mixture was stirred at 18° C. for 3 hours, quenched with water, and precipitated into methanol to give, after drying at 85° C./2mm-Hg for 16 hours, 186 grams of a clear, colorless oil, corresponding to 85% yield. NMR analysis revealed that this material was a 22:78 random copolymer of the above two monomers.

The polymer analyses were: DSC, $T_g$=–42° C.; GPC: $M_n$=15,660, $M_w$=30,640; Polydispersity=1.96; Equivalent Weight by $^1$H NMR was 9,200; Inherent viscosity=0.071; $^1$H NMR (CDCl$_3$/Freon 113) δ 0.91 (s, C$\underline{H}_3$), 3.22 (m, backbone —C$\underline{H}_2$), 3.44 (s, —C$\underline{H}_2$O), 3.79 (q, J=8.8 Hz, —C$\underline{H}_2$CF$_3$) and 3.86 (t, J=13.5 Hz, —C$\underline{H}_2$C$_3$F$_7$); $^1$H NMR CDCl$_3$/Freon 113/Trifluoroacetic anhydride) δ 0.95 (s, —C$\underline{H}_3$), 3.23 (m, backbone —C$\underline{H}_2$'S), 3.46 (s, —C$\underline{H}_2$O), 3.77 (q, J=8.6 Hz, —C$\underline{H}_2$CF$_3$), 3.87 (t, J=13.5 Hz, —C$\underline{H}_2$C$_3$F$_7$), and 4.31 (s, —C$\underline{H}_2$OCOCF$_3$); $^{13}$C NMR (CDCl$_3$/Freon 113) δ 17.3, 41.6, 41.8, 68.6 (t), 69.3.(q), 74.2, 75.6, and 75.9 (signals from carbons bearing fluorine are not included).

In a similar manner, random copolymers of above monomers in 50:50 and 75:25 ratios were also prepared. The copolymers were clear, colorless oils that were soluble in tetrahydrofuran, methylene chloride and 1,1,2-trichlorotrifluoroethane (Freon 113).

EXAMPLE B14

Copolymerization of 3-FOX and 15-FOX 3-(2,2,3,3,4,4,5,5,6,6,7,7,8,8,8-Pentadecafluorooctyloxymethyl)-3-methyloxetane with 3-(2,2,2-Trifluoroethoxymethyl)-3-methyloxetane A one-liter, three-necked, round-bottomed flask was fitted with a mechanical stirrer, nitrogen inlet/outlet tubes, a reflux condenser, a thermometer, and a constant addition funnel. The apparatus was dried with a heat gun, cooled under nitrogen to room temperature, and charged with a mixture of 0.914 grams of trimethylolpropane (TMP, 6.52 mmol), 3.1 grams of boron trifluoride tetrahydrofuranate (22 mmol), 160 milliliters of 1,1,2-trichlorotrifluoroethane and 30 milliliters of anhydrous methylene chloride. The mixture was stirred at room temperature for 30 minutes, cooled to 10° C., and then treated, dropwise, with a solution of 106 grams of 3-(2,2,2-trifluoroethoxymethyl)-3-methyloxetane (576 mmol) and 94 grams of 3-(2,2,3,3,4,4,5,5,6,6,7,7,8,8,8-pentadecafluorooctyloxymethy)-3-methyloxetane (195.2 mmol) in 40 milliliters of 1,1,2-trichlorotrifluoroethane. A mild exotherm was observed in addition of the monomer. The reaction temperature was maintained at 18° C. for 2 hours and then at 25° C. for 4 hours at which time NMR analysis of an aliquot indicated that 98 percent of the oxetane monomers were consumed. The reaction mixture was diluted with 50 milliliters of methylene chloride and 50 milliliters of 1,1,2,-trichlorotrifluoroethane, and quenched with 50 milliliters of water. The organic layer was separated, washed with two equal volumes of water, and added dropwise to a 10 fold excess of methanol at room temperature. The precipitated oil was separated and redissolved in a 50:50 mixture of methylene chloride and 1,1,2-trichlorotrifluoroethane and transferred to a 500-milliliter, round-bottomed flask. The solvent was evaporated under reduced pressure and the resulting oil was dried at 85° C./2mm-Hg for 16 hours to give 170 grams of a clear, colorless, viscous oil, corresponding to 85 percent yield. The NMR analyses of this material indicated it was a random copolymer of the above two monomers in a 74:26 ratio. The polymer analyses were: DSC, $T_g$=−40° C.; GPC: $M_n$=6,178, $M_w$=7,286, Polydispersity=1.18; Equivalent Weight by $^1H$ NMR was 3,520; Inherent viscosity was 0.065; $^1H$ NMR (CDCl$_3$) δ 0.94 (s, —C$\underline{H}_3$), 3.23 (m, backbone —C$\underline{H}_2$'S), 3.47 (s, —C$\underline{H}_2$O), 3.75 (q, J=8.6 Hz, —C$\underline{H}_2$CF$_3$) and 3.85 (t, J=13.5 Hz, —C$\underline{H}_2$C$_3$F$_7$); $^1H$ NMR (CDCl$_3$/ Trifluoroacetic anhydride) δ 1.00 (s, —C$\underline{H}_3$), 3.37 (m, backbone —C$\underline{H}_2$'S), 3.49 (s, —C$\underline{H}_2$O), 3.78 (q, J=8.6 Hz, —C$\underline{H}_2$CF$_3$), 3.96 (t, J=13.5 Hz, —C$\underline{H}_2$C$_3$F$_7$), and 4.30 (s, C $\underline{H}_2$OCOCF$_3$); $^{13}C$ NMR (CDCl$_3$) δ 17.1, 41.2, 41.3, 68.5 (t), 68.9 (q), 73.7, 75.3 and 75.5.

In a manner similar to that described above, random copolymers of above monomers in 50:50, 33:67, 25:75 and 10:90 ratios were also prepared. These copolymers were clear, colorless oils that wee soluble in a solvent mixture of methylene chloride and 1,1,2,-trichlorotrifluoroethane.

EXAMPLE B15

Copolymerization of a mixture of 13-FOX, 17-FOX and 21-FOX 3,3,4,4,5,5,6,6,7,7,8,8,8-tridecafluorooctyloxymethyl-, 3,3,4,4,5,5,6,6,7,7,8,8,9,9,10,10,10-heptadecafluorodecyloxymethyl-, and 3,3,4,4,5,5,6,6,7,7,8,8,9,9,10,10,11,11,12,12,12-heneicosafluorododecyloxymethyl-3-methyloxetanes In a manner similar to that described in Example B12, a solution of 30 grams of 13-FOX (73%), 17-FOX (24%), and 21-FOX (3%) monomers (62 mmol) in 10 milliliters of Freon 113 was added dropwise to a mixture of 300 milligrams of boron trifluoride tetrahydrofuranate (2.14 mmol) and 95 milligrams of 1,4-butanediol (1.05 mmol) in 30 milliliters of methylene chloride at 10° C. The mixture was stirred at room temperature for 24 hours, quenched with water, and precipitated in methanol to give, after drying at 80° C./2 mm-Hg for 16 hours, 24 grams of the title copolymer. Corresponding to 80 percent yield. The copolymer was a colorless, viscous oil. The analysis of the co-prepolymer was: Inherent viscosity=0.075 dL/g; GPC: $M_n$=6,639, $M_w$=9,368, Polydispersity=1.41; $^1H$ NMR (CDCl$_3$/Freon 113/TFAA) δ 0.95 (s, 3 H), 2.37 (br t, J=18.3 Hz, 2 H), 3.25 (m, 4 H), 3.35 (s, 2H), 3.71 (t, 6.0 Hz, 2 H), and 4.30 (AB, —C$\underline{H}_2$OCOCF$_3$); Equivalent Weight based on $^1H$ NMR was 2,510; $^{13}C$ NMR (CDCl$_3$,Freon 113) δ 17.35, 31.75 (5), 41.1, 41.5, 63.4, 74.1 and 74.3.

C. ELASTOMERS

The FOX prepolymers of this invention canb be cured with diisocyanates or polyisocyanates for the production of polyurethane elastomers. Detailed descriptions of the preferred method of making these elastomers are provided below.

Experimental

Mechanical properties (Stress-Strain analysis) were measured with a Model 1122 Instron tester. Static contact angles of water with the polymer surface were measured with a Goniometer using doubly distilled water. Differential scanning calorimetry (DSC) and Thermogravimetric Analysis (TGA) were performed on a DuPont 990 thermal analyzer system. DSC measurements were made at a heating rate of 10° C./min in air, whereas TGA measurements were made at a heating rate of 20° C./min in air at a flow rate of 20 mL/min. Peel strength was measured with an Instron. Chemical resistance was measured by immersing the samples in selected solvents, removing the samples from the solvent after 24 h, and measuring the change in weight and dimensions. Surface energy was measured by the method of Wu et al. Isocyanates such as isophorone diisocyanate (IPDI), saturated methylenediphenyl diisocyanate (Des-W), N-100 and N3200 were obtained from Mobay Chemical Co. Isopherone diisocyanate (IPDI), was distilled prior to polymerization. 4,4'-Methylene dianiline (MDA) and solvents were purchased from Aldrich Chemical Co., where as Jeffamine was obtained from Texaco Corporation. Isonal 93 was obtained from Dow Chemical Corporation.

EXAMPLE C1

Preparation of Poly 7-FOX/Des-W/Isonol Polyurethane Elastomer

This example illustrates the preparation of a polyurethane elastomer from the Homo-prepolymer of 3-(2,2,3,3,4,4,4-heptafluorobutoxymethyl)-3-methyloxetane (Poly 7-FOX) with the Des-W diisocyanate and the Isonol 93 cross-linker.

Note that the surface energy of the resulting 7-FOX polyurethane is 13.2 ergs/cm$^2$ which is a significant improvement over the surface energy of Teflon at 18.5 ergs/cm$^2$.

Procedure A (No solvent; casting a bulk article)

A 50 mL, 3-necked flask was dried with a heat gun under nitrogen and charged with Poly 7-FOX (10.005 g, 2.22 meq), Isonol 93 (107 mg, 1.21 meq), Des-W (469 mg, 98.5% pure, 3.50 meq), and dibutyltin dilaurate (3 mg). The contents were mixed and casted into a Teflon mold. The mixture was then degassed, placed in an oven, and cured at 65° C. for 16 h. The polymer sample was removed from the mold and characterized as follows:

| | |
|---|---|
| Nature: | Tack-free Elastomer |
| Color: | Opaque |
| Static Contact Angle (H₂O) | 117° |
| Surface Energy | 13.2 ergs/cm² |
| Mechanical Properties | |
| - Tensile Modulus | 41 psi |
| - Elongation at Break | 1308% |
| - Tensile Strength | 622 psi |
| Hardness | 7 Shore A |
| Glass Transition Temperature, DSC | −45° C. |
| Thermal Stability, TGA | 0% Wt. Loss to 260° C. |
| - Onset of major degradation | 275° C. |
| Peel Strength, EPDM Rubber | 9.5 lb/in, Adhesive Failure |
| Water Absorption | |
| - 9 days/25° C. | 0.16% by Weight Gain |
| - 16 h/100° C. | 0.28% by Weight Gain |
| Chemical Resistance | |
| - Stable | Methanol, hexane, toluene, 20% sodium hydroxide, non-leaded gasoline, & DMF |
| - Swell | THF, MTBE and Freon 113 |

EXAMPLE C2

Preparation of Poly 3/7-FOX/IPDI/MDA Polyurethane Elastomer

This example illustrates the preparation of polyurethane elastomer from a 25:75 Co-prepolymer of 3-(2,2,2-trifluoroethoxymethyl)-3-methyloxetane and 3-(2,2,3,3,4,4,4-heptafluorobutoxymethyl)-3-methyloxetane (Poly 3/7-FOX, 25:75).

Note that this Example describes polymerization in a solvent, therefore the solution can be used to prepare thin polyurethane elastomer coatings. Application of the coating may be by any conventional means including dip-coating, spray coating, etc.

Procedure B (Polymerization in solvent for a bulk or coated article)

A 50 mL, 3-necked round bottom flask fitted with a condenser, a mechanical stirrer, thermometer, and a nitrogen inlet/outlet was dried under nitrogen and charged with the title co-prepolymer (2.93 g, 0.651 meq), IPDI (0.298 g, 2.68 meq), dibutyltin dilaurate (16 mg), and anhydrous tetrahydrofuran (6 mL). The mixture was heated under reflux for 2.5 h, cooled to room temperature and treated with a solution of methylene dianiline (0.120 g, 98.5% pure, 2.38 meq) in tetrahydrofuran (1.5 mL). The resulting yellow solution was stirred at room temperature for 16 h, casted into a teflon mold*, and the solvent was slowly evaporated at room temperature to give a yellow tacky material. This material was cured at 65° C. for 24 h to give a tough, tack-free, elastomer. This material exhibited a contact angle with water of 112°. The mechanical properties of this elastomer were: tensile modulus, 48 psi; elongation at break, 941%; and tensile strength, 214 psi. The polymer sample was insoluble in methanol, toluene, ethanol and hexane, but swelled in Freon 113 and THF.

* Alternately, the substrate can be dip-coated or sprayed and cured in an oven at 65° C. for 24 h to give a thin, continuous film, tack-free coating.

EXAMPLE C3

Preparation of Poly 3/7-FOX/IPDI/TMP Polyurethane Elastomer

This example illustrates the preparation of polyurethane elastomer from a 25:75 Co-prepolymer of 3-(2,2,2-trifluoroethoxymethyl)-3-methyloxetane and 3-(2,2,3,3,4,4,4-heptafluorobutoxymethyl)-3-methyloxetane (Poly 3/7 FOX, 25:75) by Procedure A as in Example C1 and using TMP as a cross-linking agent.

A 25 mL, 3-necked flask was dried with a heat gun under nitrogen and charged with the title co-prepolymer (5.007 g, 1.35 meq), TMP (208 mg, 4.66 meq), IPDI (682 mg, 6.12 meq), and dibutyltin dilaurate (6 mg, 0.1% wt.). The contents were mixed and casted into a Teflon mold. The mixture was then degassed, placed in an oven, and cured at 65° C. for 16 h. The cured material was removed from the mold and characterized as follows:

| | |
|---|---|
| Nature: | Tack-free Elastomer |
| Color: | Opaque |
| Static Contact Angle (H₂O) | 114° |
| Surface Energy | 15.4 ergs/cm² |
| Mechanical Properties | |
| - Tensile Modulus | 34 psi |
| - Elongation at Break | 1256% |
| - Tensile Strength | 427 psi |
| Hardness | 5 Shore A |
| Glass Transition Temperature, DSC | −42° C. |
| Water Absorption | |
| - 9 days/25° C. | 0.22% by Weight Gain |
| - 6 h/100° C. | 0.25% by Weight Gain |
| Chemical Resistance | |
| - Stable | Methanol, Hexane, Toluene, 20% Sodium hydroxide, and DMF |
| - Swell | THF and Freon 113 |

EXAMPLE C4

Preparation of Poly 3-FOX/Des-W/Isonol Polyurethane Elastomer

This example illustrates the preparation of polyurethane elastomer from the homo-prepolymer of 3-(2,2,2-trifluoroethoxymethyl)-3-methyloxetane (Poly 3-FOX) by Procedure A. This Example is the same as in Example C1 except that Example C1 uses the 7-FOX.

Note that although the resulting 3-FOX polyurethane elastomer contains only 29% fluorine as compared to Teflon which has 76% fluorine, the contact angle is the same as Teflon. Further, the polyurethane elastomer of this invention is clear, making it useful for optical applications.

A 10 mL round bottomed flask was dried under nitrogen and charged with Poly 3 FOX (5.003 g, 1.25 meq), Isonol 93 (26 mg, 0.29 meq), Des-W (214 mg, 98%, 1.59 meq), and dibutyltin dilaurate (8 mg). The contents were mixed and casted into a Teflon mold. The mixture was then degassed, placed in an oven, and cured at 65° C. for 8 h. The cured material was removed from the mold and characterized as follows:

| | |
|---|---|
| Nature: | Tack-free Elastomer |
| Color | Clear, transparent |
| Static Contact Angle (H₂O) | 110° |
| Mechanical Properties | |
| - Tensile Modulus | 79 psi |
| - Elongation at Break | 926% |
| - Tensile Strength | 670 psi |
| Hardness | 11 Shore A |
| Glass Transition Temperature, DSC | −40° C. |

EXAMPLE C5

Preparation of Poly 3/15-FOX/Des-W/Isonol Polyurethane Elastomer

This example illustrates the preparation of polyurethane elastomer from a 25:75 Co-prepolymer of 3-(2,2,2-trifluoroethoxymethyl)-3-methyloxetane and 3-(2,2,3,3,4,4,5,5,6,6,7,7,8,8,8-pentadecafluorooctyloxymethyl)-3-methyloxetane (Poly 3/15 FOX, 25:75) by Procedure A.

Note that this Example shows that long side-chains on the prepolymers of this invention do not sterically inhibit polymerization. Additionally, the contact angle has increased significantly as a result of the presence of the long side-chains.

A 50 mL, 3-necked flask was dried with a heat gun under nitrogen and charged with the poly 3/15-FOX (11.003 g, 3.67 meq), Isonol 93 (74 mg, 0.83 meq), Des-W (607 mg, 98.5% pure, 4.53 meq), and dibutyltin dilaurate (5.2 mg). The contents were mixed and casted into a Teflon mold. The mixture was then degassed, placed in an oven, and cured at 65° C. for 36 h. The cured material was removed from the mold and characterized as follows:

| Nature: | Tack-free Elastomer |
|---|---|
| Color | Opaque |
| Static Contact Angle (H$_2$O) | 128° |
| Mechanical Properties | |
| - Tensile Modulus | 67 psi |
| - Elongation at Break | 1117% |
| - Tensile Strength | 344 psi |
| Hardness | 5 Shore A |
| Glass Transition Temperature, DSC | −47° C. |
| Water Absorption | |
| - 9 days/25° C. | 0.20% by Weight Gain |
| - 16 h/100° C. | 0.22% by Weight Gain |
| Chemical Resistance | |
| - Stable | Methanol, hexane, toluene, 20% sodium hydroxide carbon tetrachloride, ethanol, DMSO, non-leaded gasoline, acetic acid, 3N sulfuric acid, & DMF |
| - Swell | THF, MTBE and Freon 113 |

EXAMPLE C6

Preparation of Poly 3/13-FOX/Des-W/Isonol Polyurethane Elastomer

This example illustrates the preparation of polyurethane from a 50:50 Co-prepolymer of 3-(2,2,3,3,4,4,4-heptafluorobutoxymethyl)-3-methyloxetane and 3-(3,3,4,4,5,5,6,6,7,7,8,8,8-tridecafluorooctyloxymethyl)-3-methyloxetane (Poly 3/13 FOX, 50:50) by Procedure A.

A 25 mL round bottom flask was dried with a heat gun under nitrogen and charged with the poly 3/13-FOX (2.36 g, 0.89 meq), Isonol 93 (18 mg, 0.20 meq), Des-W (149 mg, 98.5% pure, 1.11 meq), and dibutyltin dilaurate (5.2 mg). The contents were mixed and casted into a Teflon mold. The mixture was then degassed, placed in an oven, and cured at 75° C. for 18 h. The polymer sample was removed from the mold and characterized as follows:

| Nature: | Tack-free Elastomer |
|---|---|
| Color | Opaque |
| Contact Angle (H$_2$O): | 126° |

EXAMPLE C7

Preparation of Poly 3/13/17/21-FOX/N-100 Polyurethane Elastomer

This example illustrates the preparation of polyurethane from a co-prepolymer of 3-(3,3,4,4,5,5,6,6,7,7,8,8,8-tridecafluorooctyloxymethyl)-3-methyloxetane, 3-(3,3,4,4,5,5,6,6,7,7,8,8,9,9,10,10,10-Heptadecafluorodecyloxymethyl)-3-methyloxetane, and 3-(3,3,4,4,5,5,6,6,7,7,8,8,9,9,10,10,11,11,12,12,12-Heneicosafluorododecyloxymethyl)-3-methyloxetane (Poly 3/R FOX) by Procedure A. No alcohol or amino-based cross-linking agent was used. N-100 is a polyisocyanate.

This Example represents the first time a terpolymer using commercially available alcohols is incorporated into a polymer matrix. Note the extremely high contact angle of 135° indicating very low surface energy and high hydrophobicity.

A 10 mL beaker was charged with the title terpolymer (2.003 g, 0.80 meq), N-100 (151 mg, 0.79 meq), and dibutyltin dilaurate (5.2 mg). The contents were mixed and casted into a Teflon mold. The mixture was then degassed, placed in an oven, and cured at 65° C. for 23 h. The cured material was an opaque, tack-free elastomer, that exhibited a contact angle of 135° with doubly distilled water.

EXAMPLE C8

Preparation of Poly 15-FOX/N-3200 Polyurethane Elastomer

This example illustrates the preparation of polyurethane from the homo-prepolymer of 3-(2,2,3,3,4,4,5,5,6,6,7,7,8,8,8-pentadecafluorooctyloxymethyl)-3-methyloxetane (Poly 15-FOX) by Procedure A. No cross-linking agent was used. N-3200 is a polyisocyanate.

This Example provides guidance in coating a substrate to produce a thin, continuous film, polyurethane coating. Note the extremely high contact angle of 145°.

A 10 mL beaker was charged with the title copolymer (3.200 g, 1.07 meq), N-3200 (212 mg, 1.17 meq), and dibutyltin dilaurate (3 mg). The contents were mixed, degassed, and spread on an aluminum plate (2"×0.5") with a Doctor's blade to the desired thickness of between 10 to 20 mils. The plate was placed in an oven and cured at 75° C. for 16 hours. The cured coating was tack-free, opaque and exhibited a contact angle of 145° with doubly distilled water. The contact angle of the title elastomer is compared with the contact angle of Teflon in FIG. 1.

D. FOX/THF CO-PREPOLYMERS and POLYURETHANES

Prepolymers composed of fluorinated polyether segments and hydrocarbon THF segments may be cured with di- and poly-isocyanates to produce fluorinated elastomers having exceptional hydrophobicity and good physical and mechanical properties.

The following provide by way of example the methods used to synthesize the FOX/THF coprepolymers and the -continued

| Chemical Resistance | |
|---|---|
| - Stable | Methanol, hexane, toluene, 20% Sodium hydroxide & DMF |
| - Swell | Freon 113 | synthesis of the polyurethanes of this invention. Examples D1–D5 are directed to the FOX/THF coprepolymer synthesis and Examples D6–D9 are directed to the synthesis of the FOX/THF polyurethane elastomers.

Experimental $^1$H, $^{13}$C, and $^{19}$F NMR analyses were conducted on a 300 MHz, Bruker MSL-300 spectrometer. The proton and carbon chemical shifts are recorded in ppm downfield from tetramethylsilane. Fluorine shifts are reported in ppm relative to trichlorofluoromethane. Infrared analyses were conducted on a Nicolet SX 5 spectrometer. Gel Permeation Chromatography was conducted on a Water's gel permeation chromatograph equipped with four ultrastyragel columns (100 Å, 500 Å, 1000 Å, and 10,000 Å), a refractive index detector, and a Datamodule 730. THF was used as the mobile phase. The GPC was calibrated with a set of well-characterized (i.e., $M_n$, $M_w$ are well known) polystyrene standards (Narrow Standards), and thus the number average molecular weight ($M_n$) and weight average molecular weight ($M_w$) are reported relative to polystyrene. Mechanical properties were measured with a Model 1122 Instron, and dynamic mechanical properties were measured with Model 660 Rehometrics Mechanical Spectrometer (RMS). Static contact angles of water with polymer surfaces were measured with a Goniometer using doubly distilled water. Differential scanning calorimetry (DSC) and thermogravimetric analysis (TGA), were performed on a DuPont 990 thermal analyzer system. DSC measurements were made at a heating rate of 10° C./min in air, whereas TGA measurements were made at a heating rate of 20° C./min in air at a flow rate of 20 mL/min. Surface energy was measured by the method of Wu et al. Inherent viscosity was measured in THF at a concentration of 0.50 g/dL at 25° C.

Solvents were purchased from Aldrich Chemical Co., and used without purification. Tetrahydrofuran was purified by distillation prior to polymerization. Isocyanates such as Isophorone diisocyanate (IPDI), saturated methylenediphenyldiisocyanate (Des-W), hexamethylene diisocyanate (HDI), and N-3200 (biuret of HDI) were obtained from Mobay Chemical Co., and used without further purification. Jeffamines were obtained from Texaco Oil Co., whereas heptafluorobutan-1-ol was purchased from Aldrich Chemical Co. BF$_3$THF was prepared from BF$_3$ etherate and tetrahydrofuran, and was distilled prior to use.

EXAMPLE D1

Preparation of 7-FOX/THF Co-prepolymer in 60:40 Ratio

This example illustrates the synthesis of a 60:40 co-prepolymer of 3-heptafluorobutoxymethyl-3-methyloxetane and Tetrahydrofuran (Poly 7-FOX/THF 60:40).

Note that no solvent is used in the preparation of the co-prepolymer.

A 500 mL, 4 necked flask fitted with a mechanical stirrer, condenser, thermometer, and a nitrogen inlet/outlet was charged with freshly distilled THF (27.0 g, 0.375 moles), butane-1,4-diol (0.50 g, 5.56 mmoles), and BF$_3$THF (1.90 g, 13.6 mmoles). The mixture war cooled to 8° C., and 3-heptafluorobutoxy-methyl-3-methyloxetane (7-FOX, 70.0 g, 0.246 moles) was added, dropwise, over 1.5 h. The temperature was maintained below 12° C., and the progress of the reaction was monitored by $^1$H NMR. The mixture was stirred at room temperature for 2 h and then quenched with water (100 mL). The reaction mixture was diluted with methylene chloride (100 mL) and the organic layer was washed with water (200 mL), 10% aqueous sodium bicarbonate solution (2×200 mL), water (200 mL), and brine (200 mL). The mixture was then slowly precipitated into 1.5 L of methanol, and the polymer layer was dissolved in methylene chloride (200 mL), dried (MgSO$_4$), filtered, and concentrated on a rotary evaporator to give 107 g (83%) of the title co-prepolymer, an opaque, colorless oil. GPC analysis revealed that the co-prepolymer was devoid of cyclic oligomers. The co-prepolymer was characterized as follows: $^1$H NMR (CDCl$_3$/F113) δ: 3.87 (t, J=13.4 Hz), 3.46–3.22 (m, backbone protons), 1.61 (br s), and 0.93 (s, —CH$_3$). (The ratio of 7-FOX units to THF units, as determined by $^1$H NMR analysis, was 63:37); Equivalent Weight based on TFAA end group analysis by $^1$H NMR=6,230; Equivalent Weight by p-toluenesulfonyl isocyanate/dibutyl amine titration=5,890; $^{13}$C NMR δ: 17.13, 25.56, 26.71, 41.24, 41.40, 41.55, 68.45 (t), 70.75, 71.38, 73.29, 73.93, and 75.75 (signals from carbons bearing fluorine are not included); $^{19}$F NMR δ: −81.2 (3 F), −121.0 (2 F), and −127.7 (2F); GPC: $M_n$=13,363, $M_w$=25,526, Polydispersity=1.91; Inherent Viscosity=0.125 dL/g; DSC: $T_g$=−43° C.

EXAMPLE D2

Preparation of 7-FOX/THF Co-prepolymer in 90:10 Ratio

This example illustrates the synthesis of a 90:10 co-prepolymer of 3-Heptafluorobutoxymethyl-3-Methyloxetane and Tetrahydrofuran (Poly 7-FOX/THF 90:10).

A 50 mL, 3 necked flask fitted with a mechanical stirrer, condenser, thermometer, and a nitrogen inlet/outlet was charged with methylene chloride (9 mL), 1,4 butanediol (62 mg, 0.69 mmole), and BF$_3$THF (260 mg, 1.86 mmole). After stirring at room temperature for 30 minutes, the mixture was heated to reflux for 5 minutes and then cooled to 8° C. Next, a solution of 3-heptafluorobutoxymethyl-3-methyloxetane (7-FOX, 10.2 g, 35.9 mmoles) in Freon 113 (3 mL) was added over a period of 15 minutes. The resulting mixture was stirred at room temperature for 1 h, diluted with methylene chloride (20 mL) and Freon 113 (10 mL), and quenched with water. The organic layer was washed with 10% aqueous sodium bicarbonate solution (50 mL), water (50 mL), and brine (50 mL), dried (MgSO$_4$), filtered, and concentrated on a rotary evaporator to give 10.3 g (96.3%) of the title co-prepolymer, a clear, colorless oil. GPC analysis indicated that the co-prepolymer was contaminated with ca.1.3% of cyclic tetramer. The co-prepolymer was characterized as follows: $^1$H NMR (CDCl$_3$/F113) δ 0.95 (s), 1.64 (broad), 3.25–3.37 (m), 3.48 (s), and 3.89 (t, J=13.60 Hz) (The ratio of 7-FOX units to THF units, as determined by $^1$H NMR analysis, was 90:10); Equivalent weight based on TFAA end group analysis by $^1$H NMR=6,649; $^{13}$C NMR (CDCl$_3$/F113) δ 17.08, 26.54, 26.69, 41.25, 41.41, 41.57, 41.81, 68.49 (t), 70.73, 71.39, 73.30, 73.52, 74.00, and 75.79 (signals from carbon bearing fluorines are not included due to complex splitting patterns and low peak intensities); GPC: $M_n$=11,586, $M_w$=23,991, Polydispersity=2.07; DSC, $T_g$=−41° C.

EXAMPLE D3

Preparation of 7-FOX/THF Co-prepolymer in 35:65 Ratio

This example illustrates the synthesis of a 35:65 co-prepolymer of 3-Heptafluorobutoxymethyl-3-methyloxetane and Tetrahydrofuran (Poly 7-FOX/THF 35:65).

Note that no solvent is used in this Example and that no cyclic tetramer was detected.

A 100 mL round bottomed flask fitted with a reflux condenser, nitrogen inlet/outlet, thermometer and an addition funnel was charged with freshly distilled THF (25 mL, 22.2 g, 308 mmol), BF$_3$ THF (366 mg, 2.6 mmol), and 1,4-butanediol (90 mg, 1.0 mmol). The mixture was stirred at room temperature for 10 mins, cooled to 10° C. and treated, dropwise, with 3-heptafluorobutoxymethyl-3-methyloxetane (7-FOX, 10.2 g, 35.9 mmol) over a period of 10 mins. The mixture was stirred at 10° C. for 10 mins and then at room temperature for 2 days. The progress of the reaction was monitored by $^1$H NMR. The reaction mixture was diluted with methylene chloride and Freon 113 (60:40), and then quenched with water (10 mL). The organic layer was separated and washed with water (30 mL), 10% aqueous sodium bicarbonate solution (30 mL), water (30 mL) and brine (30 mL). The organic layer was dried (MgSO4), filtered, and concentrated under reduced pressure to give 16.2 g of the title co-prepolymer, a colorless, viscous oil. GPC analysis indicated that the co-prepolymer was devoid of cyclic oligomers. The co-prepolymer was characterized as follows: $^1$H NMR (CDCl$_3$) δ 0.95 (s), 1.63–1.64 (br s), 3.24 (s), 3.42–3.48 (m), and 3.87 (t) (The ratio of 7-FOX units to THF units by $^1$H NMR was 66:34); Equivalent weight based on TFAA end group analysis by $^1$H NMR=6,104; $^{13}$C NMR 17.32, 26.93, 27.08, 41.59, 41.76, 41.95, 68.89 (t), 70.88, 71.67, 73.65, 74.34, 74.39, 76.22, and 76.57 (signals from carbon bearing fluorines are not included due to complex splitting patterns and low peak intensities); GPC: M$_n$=12,576, M$_w$=20,018, and Polydispersity=1.59.

EXAMPLE D4

Preparation of 13-FOX/THF Co-prepolymer in 50:50 Ratio

This example illustrates the synthesis of a 50:50 co-prepolymer of 3-(3,3,4,4,5,5,6,6,7,7,8,8,8-tridecafluorooctyloxymethyl)-3-methyloxetane and Tetrahydrofuran (Poly 13-FOX/THF 50:50).

This is another example of a FOX/THF co-prepolymer with the FOX monomers having long fluorinated sidechains. As in the previous Example C5, the presence of the long side-chains unexpectedly do not hinder the polymerization. Further, unlike the polymerization of the bis-monomers, no cyclic tetramers were detected. No solvent was used in this polymerization.

A 250 mL, 3-necked, round-bottom flask fitted with a condenser, a thermometer, a nitrogen inlet/outlet, and an addition funnel was charged with freshly distilled tetrahydrofuran (36 g, 0.5 mol), 1,4-butanediol (68 mg, 0.75 mmol), and boron trifluoride tetrahydrofuranate (250 mg, 1.786 mmol). The solution was cooled to 10° C. and 3-(3,3,4,4,5,5,6,6,7,7,8,8,8-tridecafluorooctyloxymethyl)-3-methyloxetane (13-FOX, 35.3 g, 78.8 mmol) was added over a period of 45 mins. The mixture was stirred at 10° C. for 3 h and then at room temperature for 16 h. $^1$H NMR of an aliquot revealed that the reaction of ca. 90% complete. The reaction mixture was then heated at reflux for 2 h, at which point NMR analysis indicated >95% completion. Water was added and the organic layer was slowly precipitated into methanol. The precipitated material was dissolved in 1:1 Freon 113/methylene chloride, dried (MgSO$_4$), filtered, and concentrated on a rotary evaporator to give 36.5 g (89%) of the title prepolymer, a viscous oil. GPC analysis of the prepolymer revealed total absence of cyclic oligomers. The prepolymer was characterized as follows: $^1$H NMR 3.67 (t), 3.42 (br s), 3.32–3.21 (m), 2.36 (tt), 1.63 (br s), and 0.93 (s). (The ratio of 13-FOX units to THF units by $^1$H NMR was 50:50); Equivalent weight based on TFAA end group analysis by $^1$H NMR=8,903; GPC: Mn=25,244, Mw=35,968, Polydispersity=1.43; $^{13}$C NMR 17.53, 26.95, 27.07, 32.07 (t), 41.30, 41.50, 41.71, 63.55, 71.0, 71.62, 71.89, 73.88, 74.41, and 75.35 (signals from carbon bearing fluorines are not included due to complex splitting patterns and low peak intensities).

EXAMPLE D5

Preparation of 15-FOX/THF Co-prepolymer in 60:40 Ratio

This example illustrates the synthesis of a 60:40 co-prepolymer of 3-(2,2,3,3,4,4,5,5,6,6,7,7,8,8,8-pentadecafluorooctyloxymethyl)-3-methyloxetane and Tetrahydrofuran (Poly 15-FOX/THF 60:40).

This is another example of a FOX/THF co-prepolymer with the FOX monomers having long fluorinated sidechains. As in the previous Examples C5 and D4, the presence of the long side-chains unexpectedly do not hinder-the polymerization. Further, unlike the polymerization of the bis-monomers, no cyclic tetramers were detected.

No solvent was used in this polymerization.

A 200 mL, 3-necked round bottomed flask fitted with a reflux condenser, nitrogen inlet/outlet, a magnetic stirring bar, a thermometer and an addition funnel was charged with anhydrous THF (18.14 g, 0.25 mol), 1,4-butanediol (25.7 mg, 0.29 mmol), and boron trifluoride tetrahydrofuranate (100 mg, 0.71 mmol). The mixture was cooled to 5° C. and 3-(2,2,3,3,4,4,5,5,6,6,7,7,8,8,8-pentadecafluorooctyloxymethyl)-3-methyloxetane (15-FOX, 20.0 g, 41.3 mmol) was added over a period of 10 mins. The mixture was stirred at room temperature for 2 days, quenched with water (2 mL), and slowly precipitated into methanol. The precipitated material was dissolved in a 1:1 mixture of methylene chloride and Freon 113, dried, filtered and concentrated on a rotary evaporator to give 17.3 g of the title co-prepolymer, a viscous, colorless oil. The ratio of the 15-FOX units to THF units, as determined by $^1$H NMR analysis, was 59:41. The co-prepolymer was characterized as follows: $^1$H NMR δ 3.89 (t, 13.5 Hz), 3.48–3.41 (m), 3.24 (s), 1.63 (s), and 0.95.(s); Equivalent Weight based on TFAA end group analysis by $^1$H NMR=9,321; $^{13}$C NMR δ 17.27, 26.86, 27.02, 41.51, 41.68, 41.85, 69.01 (t), 70.94, 71.57, 73.55, 74.18, and 76.09.

Polyurethanes from FOX/THF Co-prepolymers

EXAMPLE D6

Preparation of Poly 7-FOX/THF Based Polyurethane

This example illustrates the preparation of a polyurethane from Poly 60:40 7-FOX/THF and Des-W. Note that although the incorporation of THF into the prepolymer backbone results in 40% less fluorine than in a 7-FOX prepolymer (no THF), the contact angle and T$_g$ of the 7-FOX/THF polyurethane is comparable to the polyurethane derived from the 7-FOX prepolymer.

A 50 mL, 3-necked flask was dried with a heat gun under nitrogen and charged with poly 60:40 7-FOX/THF (11.00 g, 3.16 meq), Isonol 93 (64 mg, 0.73 m eq), Des-W (524 mg, 3.89 meq), and dibutyltin dilaurate (5 mg). The contents were mixed, casted into a Teflon mold, and degassed under reduced pressure for 15 mins. The mixture was then cured in an oven, under nitrogen, at 65° C. for 16 h. The cured material was removed from the mold and characterized as follows:

| Nature: | Opaque, Tack-free Elastomer |
|---|---|
| Contact Angle (H$_2$O) | 117° |
| Surface Energy | 13.5 ergs/cm$^2$ |
| Mechanical Properties | |
| Tensile Modulus | 53 psi |
| Elongation at Break | 1624% |
| Tensile Strength | 624 psi |
| Glass Transition Temperature, DSC | −43° C. |
| Peel Strength, EPDM Rubber Substrate | >10 lb/in, Cohesive Failure |

EXAMPLE D7

Preparation of a Coating From Poly 7-FOX/THF Polyurethane

This Example is the same as Example D6, except that it teaches the process for coating a substrate with a thin film of fluorinated polyurethane prepared from poly-7-FOX/THF (60:40), Des-W and Isonol 93.

A 50 ml, 3-necked flask was dried with a heat gun under nitrogen and charged with poly7-FOX/THF (60:40, 11.0 g, 3.16 meq)), Des-W (524 mg, 3.89 meq), Isonol 93 (64 mg, 0.73 meq) and dibutyltin dilaurate (5 mg). The contents were mixed, diluted with anhydrous THF (10 ml) and spread on a stainless steel substrate with a Doctor's blade. Alternately, the substrate can be dipped, or spray coated with the above formulation. The coated substrate was dried in a hood for 4 hours and then heated in an oven at 40° C. for 2 hours and then at 65° C. for 16 hours. The cured coating was a continuous, tack-free film, and exhibited a contact angle of 118° with doubly distilled water.

EXAMPLE D8

Preparation of Poly 7-FOX/THF Polyurethane in 35:65 Ratio

This example illustrates the preparation of a polyurethane from Poly 35:65 7-FOX/THF, Des-W and Isonol 93.

In a manner similar to that described in Example D6, a mixture of poly 35:65 7-FOX/THF (10.02 g, 2.50 meq), Isonol 93 (53 mg, 0.60 m eq), Des-W (417 mg, 98% pure, 3.10 meq), and dibutyltin dilaurate (1 drop) was cured in a Teflon mold at 65° C. for 16 h. The cured material was removed from the mold and characterized as follows:

| Nature: | Translucent, Tack-free Elastomer |
|---|---|
| Contact Angle (H$_2$O) | 108° |
| Mechanical Properties | |
| Tensile Modulus | 205 psi |
| Elongation at Break | 420% |
| Tensile Strength | 571 Psi |
| Glass Transition Temperature, DSC | −41° C. |

EXAMPLE D9

Preparation of Poly 15-FOX/THF Polyurethane

This example illustrates the preparation of a polyurethane from Poly 60:40 15-FOX/THF and N-3200. Note that the contact angle of the resulting polyurethane was very high (126°) despite dilution of the polymer with the THF segments. Further, there was no change in T$_g$. In comparison, the non-diluted 15-FOX polyurethane of Example C8 exhibited the highest contact angle ever observed of 145°.

In a manner similar to that described in Example D6, a mixture of poly 60:40 15-FOX/THF (3.0 g, 0.73 meq), N-3200 (135 mg, 0.73 meq), THF (0.5 mL), and dibutyltin dilaurate (3 mg), were cured in a Teflon mold, under nitrogen, at 75° C. for 3 days. The cured material was an opaque, tack free elastomer, with following properties: T$_g$ (DSC)=−46° C.; Contact Angle with Water=126°.

EXAMPLE D10

Preparation of Poly 13-FOX/THF Polyurethane

This example illustrates the preparation of a polyurethane from Poly 50:50 13-FOX/THF and Des-W In a manner similar to that described in Example D6, a mixture Of poly 50:50 13-FOX/THF (5.002 g, 1.50 meq), Isonol 93 (5.3 mg, 0.06 meq), Des-W (210 mg, 98% pure, 1.56 meq), and. dibutyltin dilaurate (4 mg) was cured at 65° C. for 2 days. The cured material was an opaque, tack free elastomer with following properties: Tg (DSC)=−43° C.; Contact Angle with Water=123° C.; Mechanical Properties: Tensile Modulus=35 psi, Elongation at Break=972%, Tensile Strength=487 psi.

It should be understood that various modifications within the scope of this invention can be made by one of ordinary skill in the art without departing from the spirit thereof. We therefore wish our invention to be defined by the scope of the appended claims as broadly as the prior art will permit, and in view of the specification if need be.

We claim:

1. A mono-substituted fluorinated oxetane monomer, said mono-substituted fluorinated oxetane monomer having the structure:

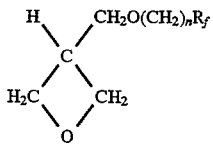

wherein:

a) n is 1 to 3;

b) R is selected from the group consisting of methyl and ethyl; and c) R$_f$ is selected from the group consisting of linear perfluorinated alkyl, linear perfluorinated isoalkyl, branched chain perfluorinated alkyl, branched chain perfluorinated isoalkyl, and oxaperfluorinated polyether having from 4 to about 60 carbons, said linear and branched alkyls and isoalkyls having from 1 to 20 carbons.

2. A monosubstituted fluorinated oxetane monomer as in claim 1, wherein said mono-substituted fluorinated oxetane monomer is a member selected from the group consisting of 3-(2,2,2-trifluoroethoxymethyl)-3-methyloxetane; 3-(2,2,3, 3,4,4,4-heptafluorobutoxymethyl)-3-methyloxetane; 3-(2,2, 3,3,4,4,5,5,6,6,7,7,8,8,8-pentadecafluorooctyloxymethyl)-3-methyloxetane; 3-(3,3,4,4,5,5,6,6,7,7,8,8,8-tridecafluorooctyloxymethyl)-3-methyloxetane; 3-(3,3,4,4, 5,5,6,6,7,7,8,8,9,9,10,10,10-heptadecafluorodecyloxymethyl)-3-methyloxetane; and 3-(3,3,4,4,5,5,6,6,7,7,8,8,9,9,10,10,11,11,12,12,12-heneicosafluorododecyloxymethyl)-3-methyloxetane.

3. A mono-substituted fluorinated oxetane (FOX) monomer, said mono-substituted fluorinated oxetane monomer produced by the process comprising the steps of:

a) providing a mono-substituted oxetane premonomer having the structure:

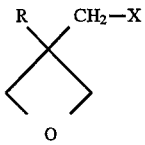

where R is selected from the group consisting of methyl and ethyl and X is a leaving group selected from the group consisting of bromo, chloro, iodo and aryl sulfonate, said mono-substituted oxetane premonomer being diluted in a solvent to provide a mono-substituted oxetane premonomer solution;

b) suspending a dispersion of a strong base in an aprotic solvent to provide a strong base suspension;

c) adding a fluorinated alcohol to said strong base suspension to produce a fluorinated alkoxide solution, said fluorinated alcohol having the structure:

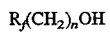

where n is 1–3 and $R_f$ is a linear or branched chain fluorinated alkyl or isoalkyl having from 1 to 20 carbons, or an oxaperfluorinated polyether having from 4 to about 60 carbon atoms; and d) adding said mono-substituted oxetane premonomer solution to said fluorinated alkoxide solution while heating the reaction mixture to a temperature of from about 50° C. to about 125° C. to permit a displacement reaction, whereby the fluorinated alkoxide displaces said leaving group to produce said mono-substituted fluorinated oxetane monomer.

4. A mono-substituted FOX monomer produced by the process as in claim 3 which includes the steps of:

a) quenching the displacement reaction upon consumption of the starting materials; and b) separating said mono-substituted fluorinated oxetane monomer product from the reaction mixture.

5. A mono-substituted FOX monomer produced by the process as in claim 3, wherein:

said fluorinated alcohol is selected from the group consisting of trifluoroethanol, heptafluorobutanol, pentadecafluorooctanol, tridecafluorooctanol and other fluorinated alcohols having the following formulas:

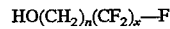
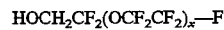
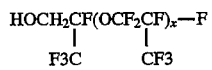

wherein n is 1 to 3 and x is 1 to 20 and mixtures thereof.

6. A mono-substituted FOX monomer produced by the process as in claim 5, wherein:

said strong base is selected from the group consisting of sodium hydride, potassium hydride, potassium t-butoxide, calcium hydride, sodium hydroxide, potassium hydroxide, $NaNH_2$, n-butyl lithium and lithium diisopropylamide.

7. A mono-substituted FOX monomer produced by the process as in claim 6, wherein:

said solvent is selected from the group consisting of dimethylformamide (DMF), dimethylacetamide, DMSO, hexamethylene phosphoramide (HMPA) and mixtures thereof.

8. A mono-substituted FOX monomer produced by the process as in claim 7, wherein:

said temperature is from about 75° to about 85° C.

9. A mono-substituted FOX monomer produced by the process as in claim 4, wherein said FOX monomer is a member selected from the group consisting of 3-(2,2,2-trifluoroethoxymethyl)-3-methyloxetane; 3-(2,2,3,3,4,4,4-heptafluorobutoxymethyl)-3-methyloxetane; 3-(2,2,3,3,4,4,5,5,6,6,7,7,8,8,8-pentadecafluorooctyloxymethyl)-3-methyloxetane; 3-(3,3,4,4,5,5,6,6,7,7,8,8,8-tridecafluorooctyloxymethyl)-3-methyloxetane; 3-(3,3,4,4,5,5,6,6,7,7,8,8,9,9,10,10,10-heptadecafluorodecyloxymethyl)-3-methylxetane; 3-(3,3,4,4,5,5,6,6,7,7,8,8,9,9,10,10,11,11,12,12,12-heneicosafluorododecyloxymethyl)-3-methyloxetane; and mixtures thereof.

10. A mono-substituted fluorinated monomer produced by the process comprising the steps of:

a) providing a mono-substituted oxetane premonomer having the structure:

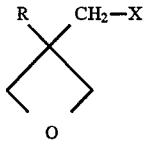

where R is selected from the group consisting of methyl and ethyl, and X is a leaving group selected from the group consisting of bromo, chloro and iodo, said mono-substituted oxetane premonomer being dissolved in water to provide an aqueous mixture of said mono-substituted oxetane premonomer;

b) charging a reaction vessel with said aqueous mixture of said mono-substituted oxetane premonomer, a fluoroalcohol, a phase transfer catalyst and a strong base to form a reaction mixture, said fluoroalcohol having the structure:

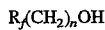

where n is 1–3 and $R_f$ is a linear or branched chain fluorinated alkyl or isoalkyl having from 1 to 20 carbons, or an oxaperfluorinated polyether having from 4 to about 60 carbon atoms;

c) heating said reaction mixture to a temperature of 80°–85° C. until the reaction is complete and forms said FOX monomer as an organic layer;

d) cooling said reaction mixture; and e) separating said mono-substituted fluorinated oxetane monomer as an organic layer from the aqueous reaction mixture.

11. A mono-substituted fluorinated monomer produced by the process of claim 10 wherein:

said phase transfer catalyst is selected from the group consisting of tetrabutylammonium bromide, tetraethylammonium bromide, trimethylbutylammonium bromide, tetramethylammonium iodide, cetyltributylammonium bromide, crown ethers, glycols and mixtures thereof.

12. A mono-substituted fluorinated monomer produced by the process of claim 11, wherein:

said fluorinated alcohol is selected from the group consisting of trifluoroethanol, heptafluorobutanol, pentadecafluorooctanol, tridecafluorooctanol and other fluorinated alcohols having the following formulas:

$$HO(CH_2)_n(CF_2)_x-F \qquad \text{a);}$$

$$HOCH_2CF_2(OCF_2CF_2)_x-F \qquad \text{b);}$$

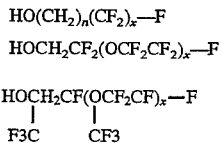  c);

wherein n is 1 to about 3 and x is 1 to about 20 and mixtures thereof.

13. A mono-substituted fluorinated monomer produced by the process of claim 12, wherein:

said strong base is selected from the group consisting of sodium hydroxide and potassium hydroxide, calcium hydroxide, magnesium hydroxide, tetrabutylammonium hydroxide and mixtures thereof.

14. A mono-substituted fluorinated monomer produced by the process of claim 13, wherein:

said strong base is potassium hydroxide and said phase transfer catalyst is tetrabutylammonium bromide.

15. A mixture of mono-substituted fluorinated oxetane monomers, said mono-substituted fluorinated oxetane monomers being selected from the group consisting of 3-(2,2,2-trifluoroethoxymethyl)-3-methyloxetane; 3-(2,2,3,3,4,4,4-heptafluoro-butoxymethyl)-3-methyloxetane; 3-(2,2,3,3,4,4,5,5,6,6,7,7,8,8,8-pentadecafluoro-octyloxymethyl)-3-methyloxetane; 3-(3,3,4,4,5,5,6,6,7,7,8,8,8-tridecafluoro-octyloxymethyl)-3-methyloxetane; 3-(3,3,4,4,5,5,6,6,7,7,8,8,9,9,10,10,10-heptadecafluorodecyloxymethyl)-3-methyloxetane; and 3-(3,3,4,4,5,5,6,6,7,7,8,8,9,9,10,10,11,11,12,12,12-heneicosafluorododecyloxymethyl)-3-methyloxetane.

* * * * *

UNITED STATES PATENT AND TRADEMARK OFFICE
CERTIFICATE OF CORRECTION

PATENT NO. : 5,654,450

DATED : August 5, 1997

INVENTOR(S) : Aslam A. Malik and Thomas G. Archibald

It is certified that error appears in the above-identified patent and that said Letters Patent is hereby corrected as shown below:

```
On the title page, item [54] and column 1, lines 1-2, change the
title to read:
MONO-SUBSTITUTED FLUORINATED OXETANE MONOMERS--.
```

Signed and Sealed this

Twentieth Day of January, 1998

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,654,450

DATED : August 5, 1997

INVENTOR(S) : Aslam A. Malik and Thomas G. Archibald

It is certified that error appears in the above-indentified patent and that said Letters Patent is hereby corrected as shown below:

Column 15, line 5, change the structure to read:

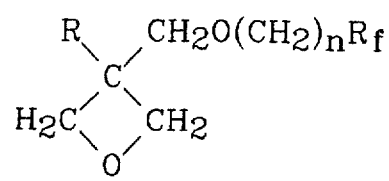

Column 15, line 9, change "Where" to -- where -- ;

Claim 1, column 56, line 40, change the structure to read:

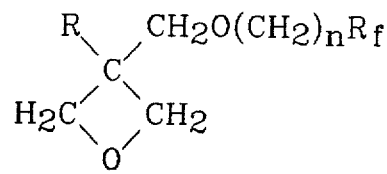

UNITED STATES PATENT AND TRADEMARK OFFICE
CERTIFICATE OF CORRECTION

PATENT NO. : 5,654,450

DATED : August 5, 1997

INVENTOR(S) : Aslam A. Malik and Thomas G. Archibald

It is certified that error appears in the above-indentified patent and that said Letters Patent is hereby corrected as shown below:

Claim 5, column 57, lines 57-59, change the structure to read:

$$\begin{array}{c} \text{HOCH}_2\text{CF}(\text{OCF}_2\text{CF})_x\text{-F} \\ | \quad\quad\quad | \\ \text{F}_3\text{C} \quad\quad \text{CF}_3 \end{array}$$

Claim 12, column 59, lines 11-12, change the structure to read:

$$\begin{array}{c} \text{HOCH}_2\text{CF}(\text{OCF}_2\text{CF})_x\text{-F} \\ | \quad\quad\quad | \\ \text{F}_3\text{C} \quad\quad \text{CF}_3 \end{array}$$

Signed and Sealed this

Twenty-fifth Day of August, 1998

*Attest:*

BRUCE LEHMAN

*Attesting Officer*   *Commissioner of Patents and Trademarks*